US005496267A

United States Patent [19]
Drasler et al.

[11] Patent Number: 5,496,267
[45] Date of Patent: Mar. 5, 1996

[54] ASYMMETRIC WATER JET ATHERECTOMY

[75] Inventors: William J. Drasler, Minnetonka; Robert G. Dutcher, Maple Grove; Mark L. Jenson, Greenfield; Joseph M. Thielen, Buffalo; Emmanuil I. Protonotarios, Brooklyn Park, all of Minn.

[73] Assignee: Possis Medical, Inc., Minneapolis, Minn.

[21] Appl. No.: 610,846

[22] Filed: Nov. 8, 1990

[51] Int. Cl.$^6$ .................................................. A61B 17/20
[52] U.S. Cl. .................................................. 604/22; 606/159
[58] Field of Search .................................. 604/22, 43, 35; 606/159, 167

[56] References Cited

U.S. PATENT DOCUMENTS

| | | |
|---|---|---|
| 1,902,418 | 11/1931 | Pilgrim . |
| 3,358,677 | 12/1967 | Sheldon .................................. 604/22 |
| 3,930,505 | 1/1976 | Wallach .................................. 604/22 |
| 4,631,052 | 12/1986 | Kensey .................................. 606/159 |
| 4,690,672 | 9/1987 | Veltrup .................................. 604/22 |
| 4,747,821 | 5/1988 | Kensey et al. ......................... 604/22 |
| 4,790,813 | 12/1988 | Kensey .................................. 604/22 |
| 4,842,579 | 6/1989 | Shiber .................................. 604/22 |
| 4,898,574 | 2/1990 | Uchiyama et al. ..................... 604/22 |
| 4,913,698 | 4/1990 | Ito et al. ............................... 604/22 |
| 4,950,238 | 8/1990 | Sullivan ................................ 604/22 |
| 5,037,431 | 8/1991 | Summers et al. ....................... 604/22 |
| 5,135,482 | 8/1992 | Neracher .............................. 604/22 |

FOREIGN PATENT DOCUMENTS

| | | |
|---|---|---|
| 0232678 | 12/1986 | European Pat. Off. . |
| 0329492 | 2/1989 | European Pat. Off. . |
| 3421390 | 12/1985 | Germany . |
| 3715418A1 | 11/1987 | Germany . |
| 1085639 | 3/1989 | Japan . |
| WO8804157 | 6/1988 | WIPO . |
| WO9005493 | 5/1990 | WIPO . |

Primary Examiner—Stephen C. Pellegrino
Assistant Examiner—Michael Rafa
Attorney, Agent, or Firm—Hugh D. Jaeger

[57] ABSTRACT

A technique for ablation and removal of plaque deposits from the arterial, venous, vascular graft or other tissue wall of a patient. Ablation is accomplished by directing a high pressure jet of sterile saline solution at the plaque deposit. The high pressure jet is located at the distal end of a catheter which is advanced through the vascular system to the site of the plaque deposit. Removal of the debris is via an evacuation lumen within the catheter.

The arterial wall is protected from damage by the catheter design which directs the high pressure jet towards a portion of the distal end of the catheter which serves as a target. The distal end of the catheter is placed such that the plaque or other deposit to be ablated is positioned between the high pressure jet and the target.

An optional ultrasonic transducer array located adjacent the high pressure jet and the evacuation lumen permits the attending physician to monitor the procedure.

A balloon may be used to hold the catheter against the deposit allowing it to protrude into the ablation jet and be removed from the vessel.

33 Claims, 50 Drawing Sheets

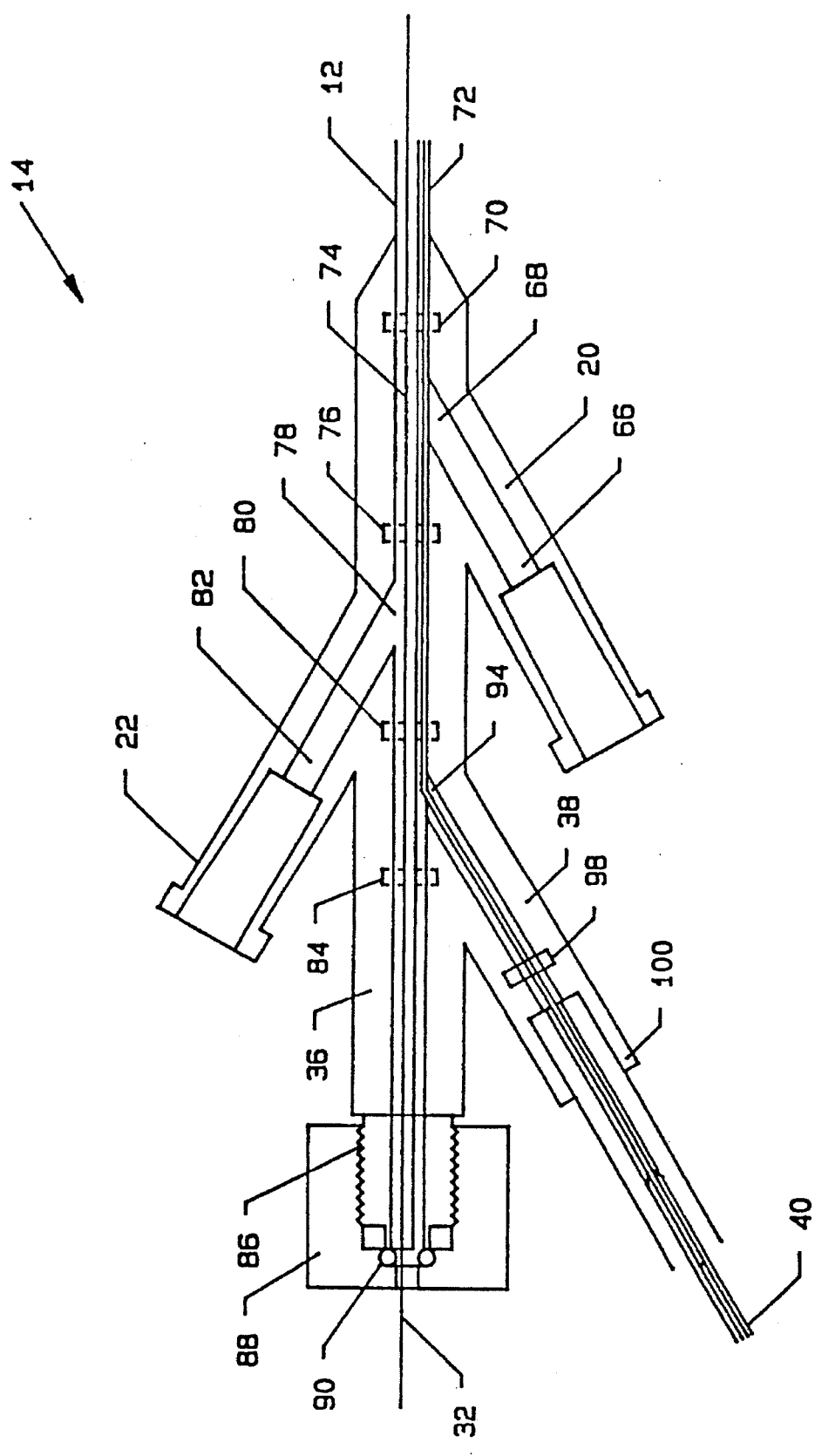

5,496,267

ASYMMETRIC WATER JET ATHERECTOMY

CROSS REFERENCE TO CO-PENDING APPLICATIONS.

This application is related to U.S. patent application Ser. No. 07/563,313, entitled Thrombectomy Method and Device, filed Aug. 6, 1990, now abandoned in the name of William J. Drasler et al., and assigned to the assignee of the present invention and incorporated herein by reference.

BACKGROUND OF THE INVENTION

1. Field of the Invention

The present invention generally relates to medical devices, and more particularly, relates to medical devices for ablation of undesirable deposits within the body of a patient.

2. Description of the Prior Art

Procedures and apparatus have been developed for ease in removing tissue and various deposits. U.S. Pat. No. 4,790,813 issued to Kensey and U.S. Pat. No. 4,842,579 issued to Shiber describe techniques for the removal of plaque deposited in arteries by mechanical ablation using rotating cutting surfaces. These relatively traumatic approaches are directed to the treatment and removal of very hard substances.

Pressurized fluids have also been used in the past to flush undesirable substances from body cavities. U.S. Pat. No. 1,902,418 describes such a system for flushing body cavities of domesticated animals. The more modern references tend to use vacuum rather than gravity as the primary means for removal of the deposits or tissue and relatively low fluid pressures for ablation.

U.S. Pat. No. 3,930,505 issued to Wallach describes a surgical apparatus for the removal of tissue from the eye of a patient. As with similar systems, Wallach uses a relatively low pressure jet of water (i.e. 15 to 3500 psi) to disintegrate the tissue, and a suction pump to perform the actual removal.

A similar approach applied to the cardiovascular system is discussed in U.S. Pat. No. 4,690,672 issued to Veltrup. Veltrup also provides a much lower pressure jet of water (i.e. less than 450 psi) to ablate the deposits. As with Wallach, Veltrup uses a vacuum pump for evacuation of the fragments. It seems apparent that the prior art uses only relatively low pressure jets for safety reasons.

SUMMARY OF THE INVENTION

The present invention overcomes the disadvantages of the prior art by providing a catheter for the ablation and removal of hardened deposits within the cardiovascular system, vascular grafts, ureters, fallopian tubes, and other tubular tissues or cavities within the body using a high pressure jet of sterile saline. The high pressure jet is located at the distal end of a catheter which is advanced through the arterial system to the location of the deposit. The stream of high pressure sterile saline ablates the deposit upon contact. The resulting fragments are removed through an evacuation lumen. The force of the jet on the evacuation lumen serves as a pump to remove the fragments through the catheter as positive pressure; evacuation does not require a vacuum.

The procedure is rendered inherently safe by directing the high pressure jet toward a target also located at the distal end of the catheter. In this way the vessel wall is protected from inadvertent damage from a misdirected high pressure stream of saline solution.

In operation, the deposit to be ablated and removed is positioned in between the high pressure jet and the target. A number of configurations are useful. The jet may be located proximal of the target and be directed distally. Alternatively, the jet may be directed proximally and be located distal of the target. With either configuration, the jet may be directed parallel to the longitudinal axis of the artery. In the alternative, the jet may have a component which projects radially outward or radially inward, wherein the target is located closer or farther from the central axis than the high pressure jet.

Other options include multiple high pressure jets. To improve monitoring possibilities during the procedure, an ultrasonic transducer array may be appropriately positioned at the distal end of the catheter. The transducer array may be directed toward the deposit or toward a mirror directed toward the deposit. An angioscope or other diagnostic device may also be used with the catheter to identify the presence of plaque or thrombus. The catheter may provide a separate lumen for passage of such devices, or the lumen may also be used for evacuation of particulate material.

A distal balloon is used to hold the catheter to one side of the vessel for removal of the deposit from that wall. This deposit ablation and removal forms the atherectomy function of the catheter. An additional balloon may also be placed on the catheter to provide dilatation of the vessel following deposit removal. This second balloon provides an angioplasty function for the catheter.

An additional passage can be provided for flushing the vessel, infusion of drugs, and injecting contrast medium for visualization. The evacuation lumen can be used for these functions.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 2A is a close-up sectioned view of manifold 14;

DETAILED DESCRIPTION OF THE PREFERRED EMBODIMENTS

Figure 1A:
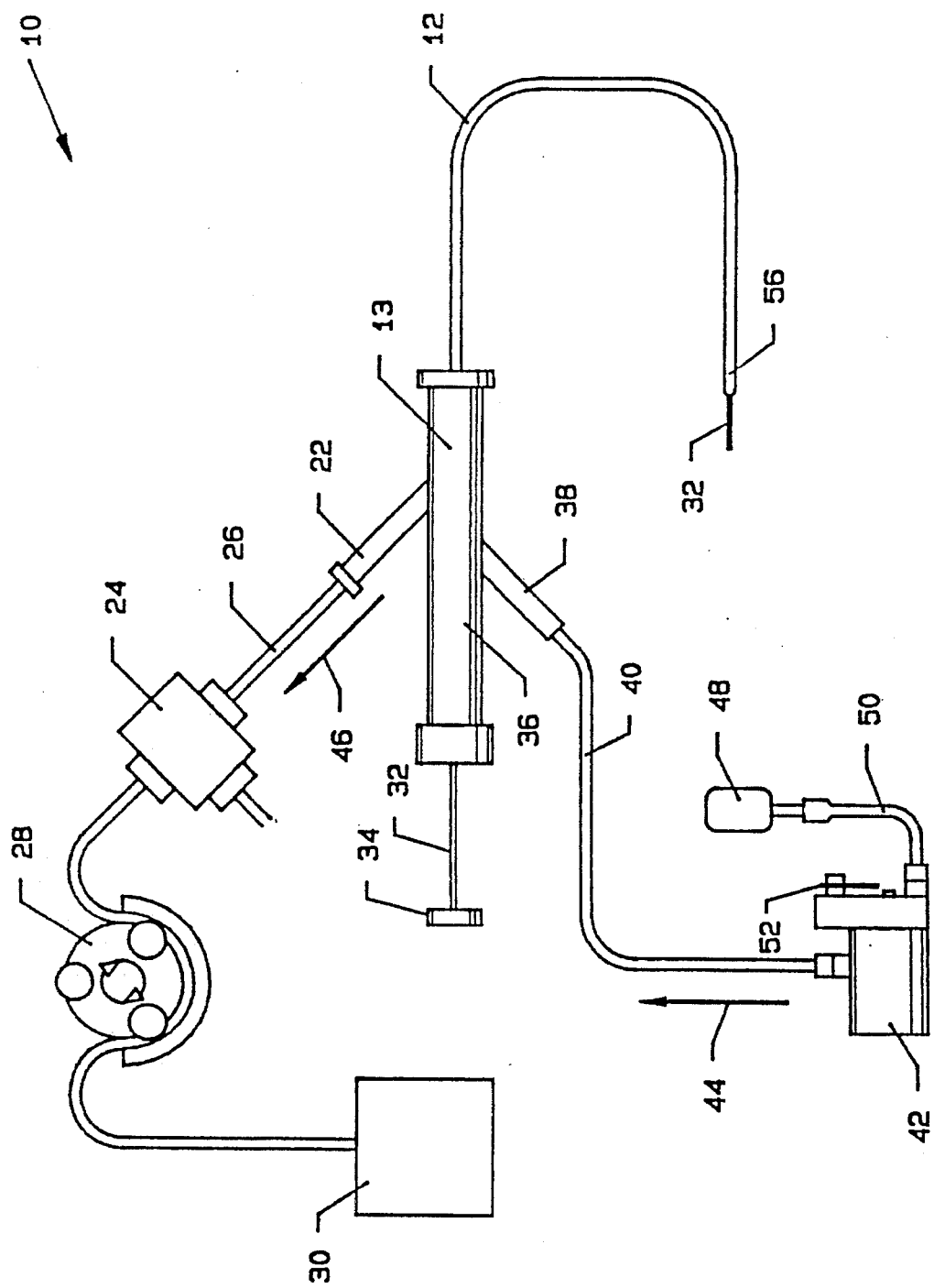
FIG. 1A is a plan view of an atherectomy system employing the present invention.

FIG. 1A is a plan view of an atherectomy catheter system 10 employing the present invention. Catheter 12 is introduced into an artery of the patient at a convenient location, usually the femoral artery. Distal end 56 is advanced to the site of the deposit to be ablated. Ordinarily, this site will have been previously identified using a suitable diagnostic procedure such as angiography. After location at the site of the deposit, the apparatus at distal end 56 of catheter 12 serves to ablate and remove the deposit as explained in more detail below.

Manifold 13 sealingly couples to the proximal end of catheter 12 and serves to provide separate access to the various lumens of catheter 12. Main branch 36 of manifold 13 sealingly couples to guide wire 32 to assist in positioning catheter 12 in the manner known in the art. Positioning knob 34 assists the medical attendant in this procedure.

Secondary branch 38 of manifold 13 permits access to catheter 12 to supply the sterile saline solution under high pressure. Hypo tubing 40 is drawn from stainless steel to have the strength to handle the pressures up to 50,000 psi and yet remain flexible enough to be positioned transarterially. Typical pressure is 30,000 psi within the range of 5,000 to 50,000 psi. Hypo tubing 40 traverses the entire length of catheter 12 from distal end 56 to secondary branch 38. Preferably and not by way of limitation, sterile saline is supplied by disposable saline solution bag 48. Low pressure tubing 50 conveys the sterile saline solution to high pressure piston pump 42. After pressurization by high pressure piston pump 42 of typically about 30,000 psi, the sterile saline solution is transported in the direction of arrow 44 through hypo tubing 40 to distal end 56 of catheter 12. Safety monitor 52 functions to shut off high pressure piston pump 42 if a failure occurs.

Secondary branch 22 of manifold 13 is coupled to the evacuation lumen of catheter 12. Fragments of the ablated deposit are channeled from secondary branch 22 through low pressure tubing 26 in the direction of arrow 46. Safety monitor 24 ensures that the volume of effluent and pressures within the system are maintained within allowable tolerances. Peristaltic pump 28 meters the rate at which effluent is evacuated to disposable bag 30. The environment in which the ablation procedure occurs is greater than one atmosphere due to the impingement of the jet on the evacuation lumen. Peristaltic pump 28 meters evacuation of the effluent without ever creating a vacuum.

Figure 1B:
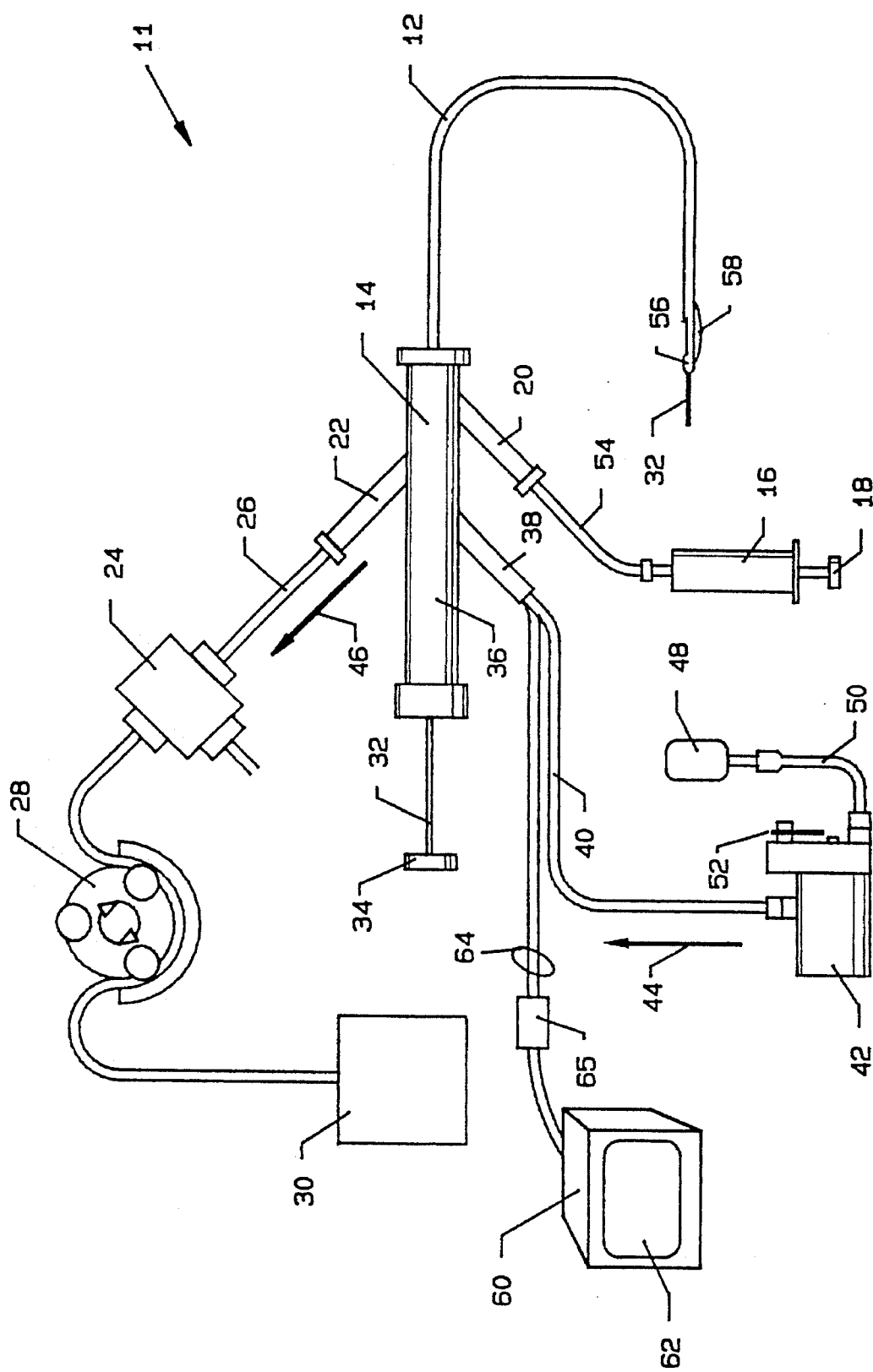
FIG. 1B is a plan view of an atherectomy system having ultrasonic monitoring.

FIG. 1B is a plan view of an alternative embodiment of the present invention. This catheter system 11 includes all of the features of catheter system 10 and further includes an inflatable distal balloon and ultrasonic monitoring.

Distal balloon 58 may be inelastic, such as those used in balloon dilatation. The balloon serves to hold the catheter close to one side of the vessel and force the plaque, thrombus, or atheromatous material to protrude into the pathway of the saline jet(s). An additional balloon (not shown) may be located on the distal end of the catheter to serve as a vessel dilatation balloon to be used after removal of the deposited material.

In the alternative embodiment, manifold 13 (see also FIG. 1A) is replaced with manifold 14 having additional secondary branch 20. The inflation lumen of catheter 12, which is coupled to distal balloon 58, is sealingly coupled through secondary branch 20 and flexible tubing 54 to balloon inflation device 16. In this way, distal movement of thumb plunger 18 causes inflation of distal balloon 58.

An additional feature of the alternative embodiment is ultrasonic monitor 60 which is coupled via cable 64 to an ultrasonic transducer array (not shown in this view) located at distal end 56. Medical personnel may view the ablation procedure on screen 62 of ultrasonic monitor 60.

FIG. 2A is a longitudinal sectioned view of manifold 14. It is preferably molded from a rigid plastic as two halves which are bonded together and are adhesively coupled at points 70, 76, 80, 84, 98, and 100. Catheter 12 is sealingly coupled to the distal end of manifold 14 using known techniques.

Lumen 82 of secondary branch 22 is sealingly coupled to evacuation lumen 74 at point 78. In most embodiments, evacuation lumen 74 will be the largest lumen of catheter 12. Evacuation lumen 74 may also be coupled to main branch 36. Compression nut 88 attaches via threads 86 to compress o-ring 90 to sealingly engage guide wire 32. During initial positioning of catheter 12, guide wire 32 may be located within evacuation lumen 74.

Lumen 72 contains hypo tubing 40 which enters secondary branch 38, bends obliquely at point 94 and extends the length of lumen 72 to distal end 56.

Also, lumen 72 is used for inflating distal balloon 58. To accomplish this, lumen 66 of secondary branch 20 is coupled to lumen 72 at point 68. Fluid used to inflate balloon 58 (see also FIG. 1B) is forced through lumen 72 in that space not occupied by hypo tubing 40.

Figure 2B:
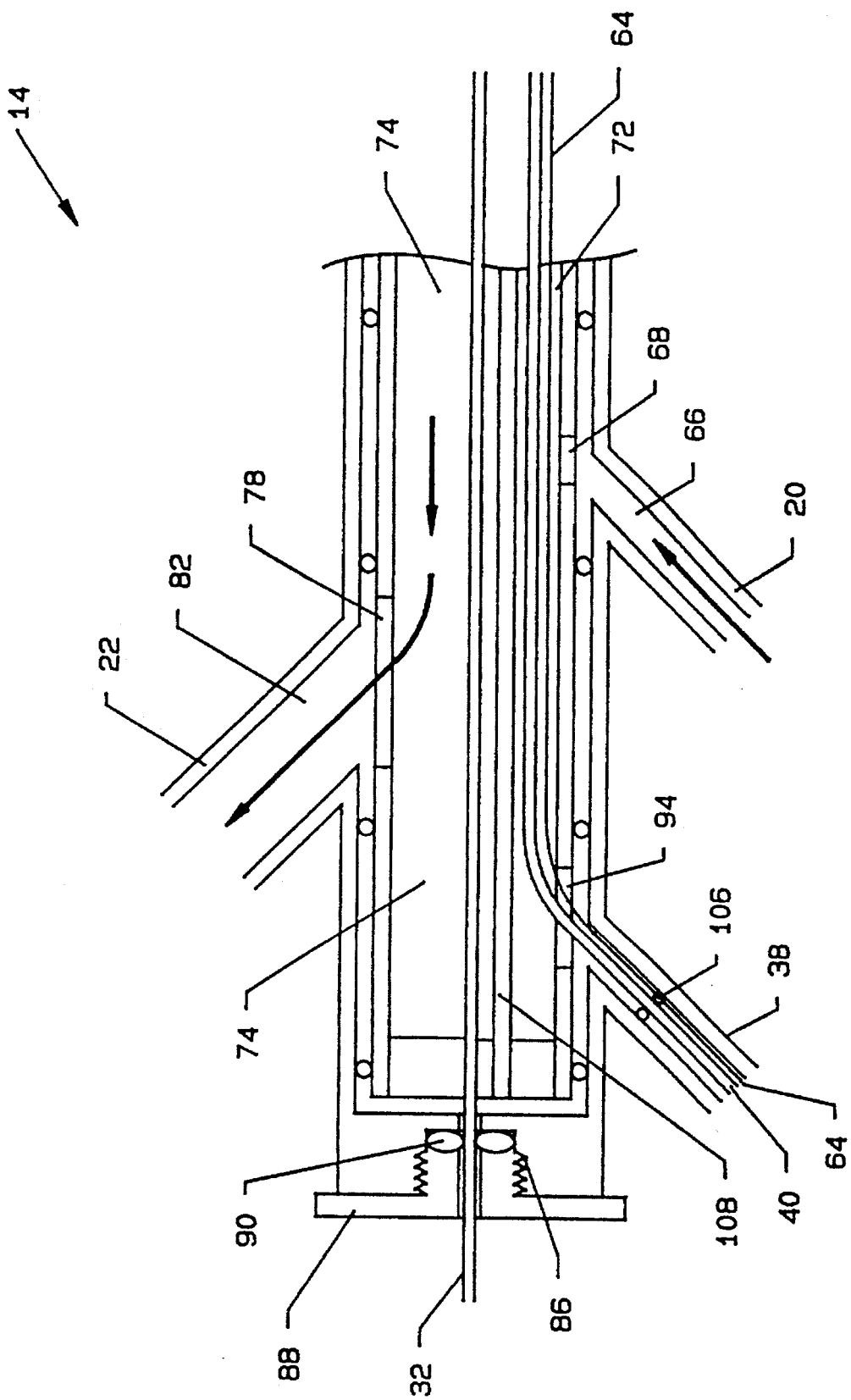
FIG. 2B is a functional view of manifold having ultrasonic monitoring.

FIG. 2B is a conceptualized view of the operation of manifold 14 wherein all referenced elements are as previously described. In this view it can be seen that septum 108 serves to separate evacuation lumen 74 from lumen 72. Flexible seal 106 seals secondary branch 38 against the walls of hypo tubing 40.

Figure 3A:
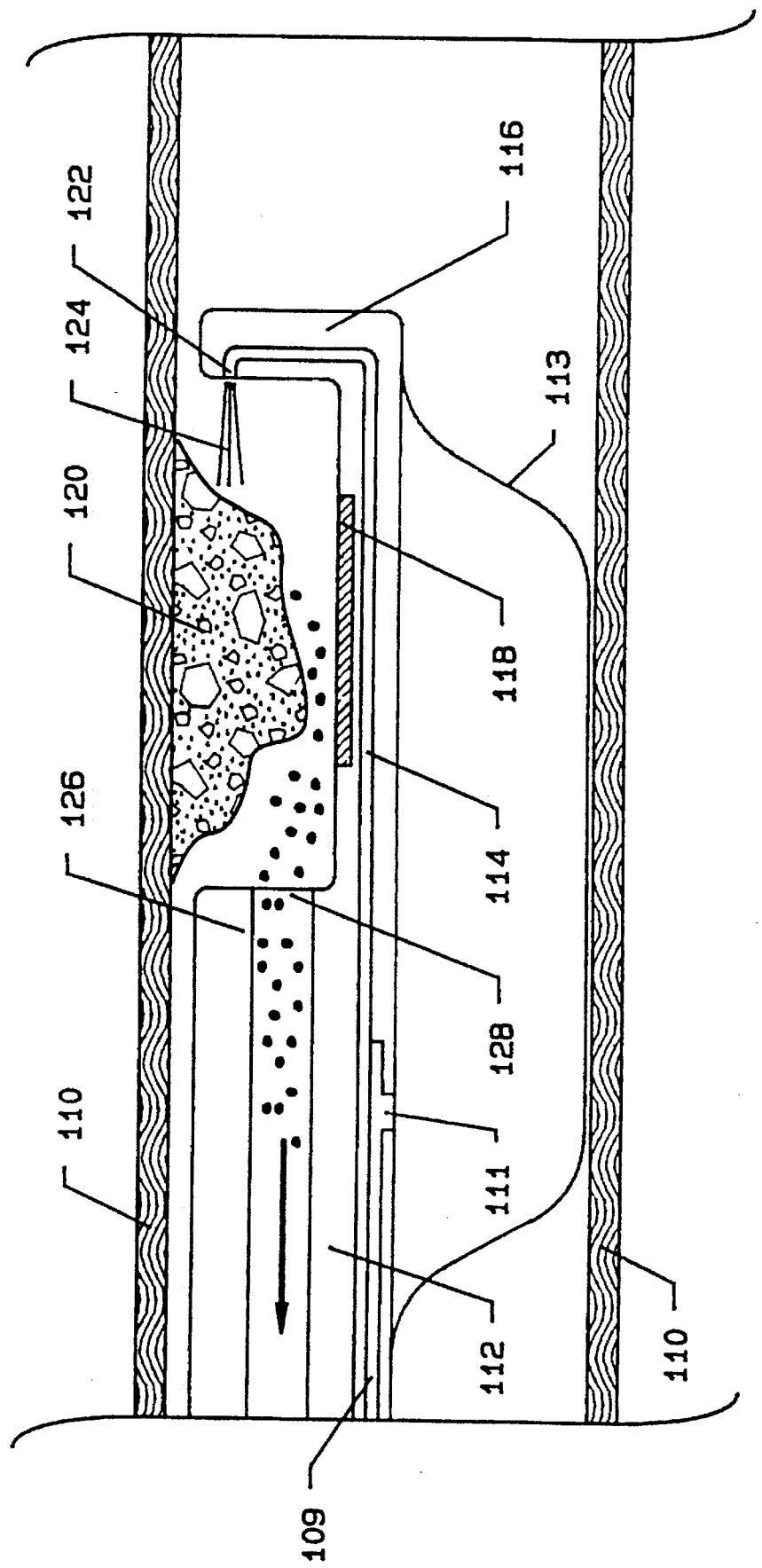
FIG. 3A is a conceptual view of the operation of an atherectomy device having a distal jet and proximal target.

FIG. 3A is a conceptual view of the operation of the distal end of an atherectomy catheter shown partially cut away. In the embodiment shown, single high pressure jet 122 is positioned at the distal end 116 of the catheter and is directed in a proximal direction. Evacuation lumen 128 of the catheter provides the target for high pressure jet 122 ensuring that high pressure saline stream 124 cannot directly contact the walls of artery 110.

Distal end of hypo tubing 114 is bent as shown to supply high pressure jet 122. Main catheter body 112 is narrowed near its distal end 116 to provide access to deposit 120. Balloon inflation lumen 109 is connected to balloon inflation port 111 to provide access for inflation of balloon 113. The balloon holds the catheter against the deposit on the opposite wall for ablation and removal.

To ablate deposit 120, the catheter must be positioned such that deposit 120 is located between wall 126 and high pressure jet 122 as shown. As deposit 120 is ablated by high pressure saline stream 124, particles are evacuated by evacuation lumen 128 as shown. These particles are propelled proximally by the stagnation pressure formed at the distal port of evacuation lumen 128 from the action of high pressure saline stream 124.

An optional ultrasonic transducer array 118 may be used to monitor the ablation and removal operation (see also FIG. 1B). This feature is addressed in more detail below.

Figure 3B:
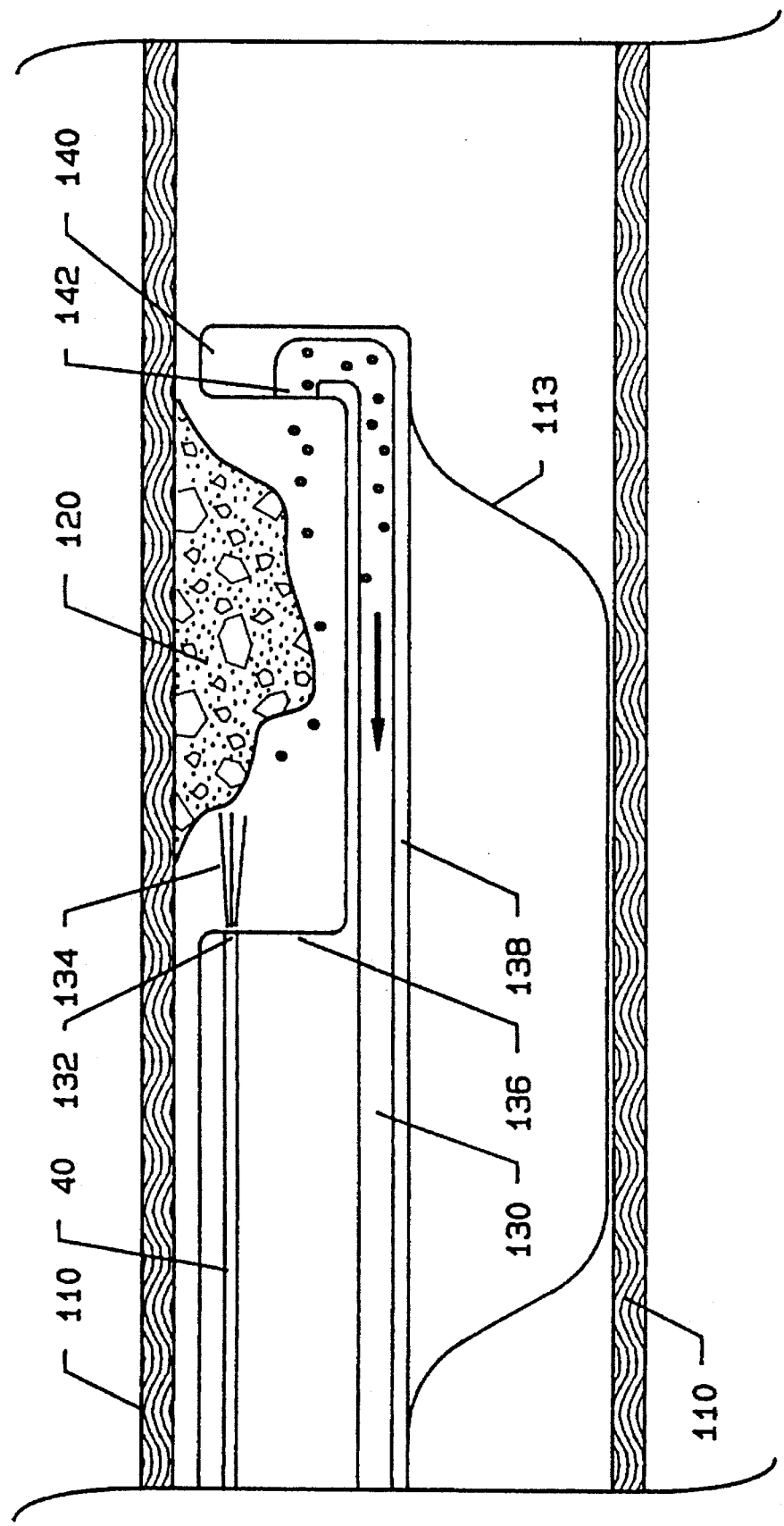
FIG. 3B is a conceptual view of the operation of an atherectomy device having a proximal jet and distal target.

FIG. 3B is a conceptual view of the operation of an alternative embodiment of an atherectomy catheter. This embodiment features wall 136 having single high pressure jet 132 which generates a high pressure saline stream 134 directed distally. Distal end 140 of the catheter operates as the target to protect the walls of artery 110 from damage by impingement of high pressure saline stream 134.

This configuration permits the distal end of hypo tubing 40 to remain straight and without any bends. However, evacuation lumen 130 must be sufficiently small to fit within narrowed portion 138 of the catheter and must bend 180 degrees within the distal end 140 in the region of point 144 to position evacuation port 142 for receipt of the particles to be removed. This embodiment may have an optional ultrasonic monitor array, although none is shown. Balloon 113 is inflated and used as previously discussed.

Figure 3C:
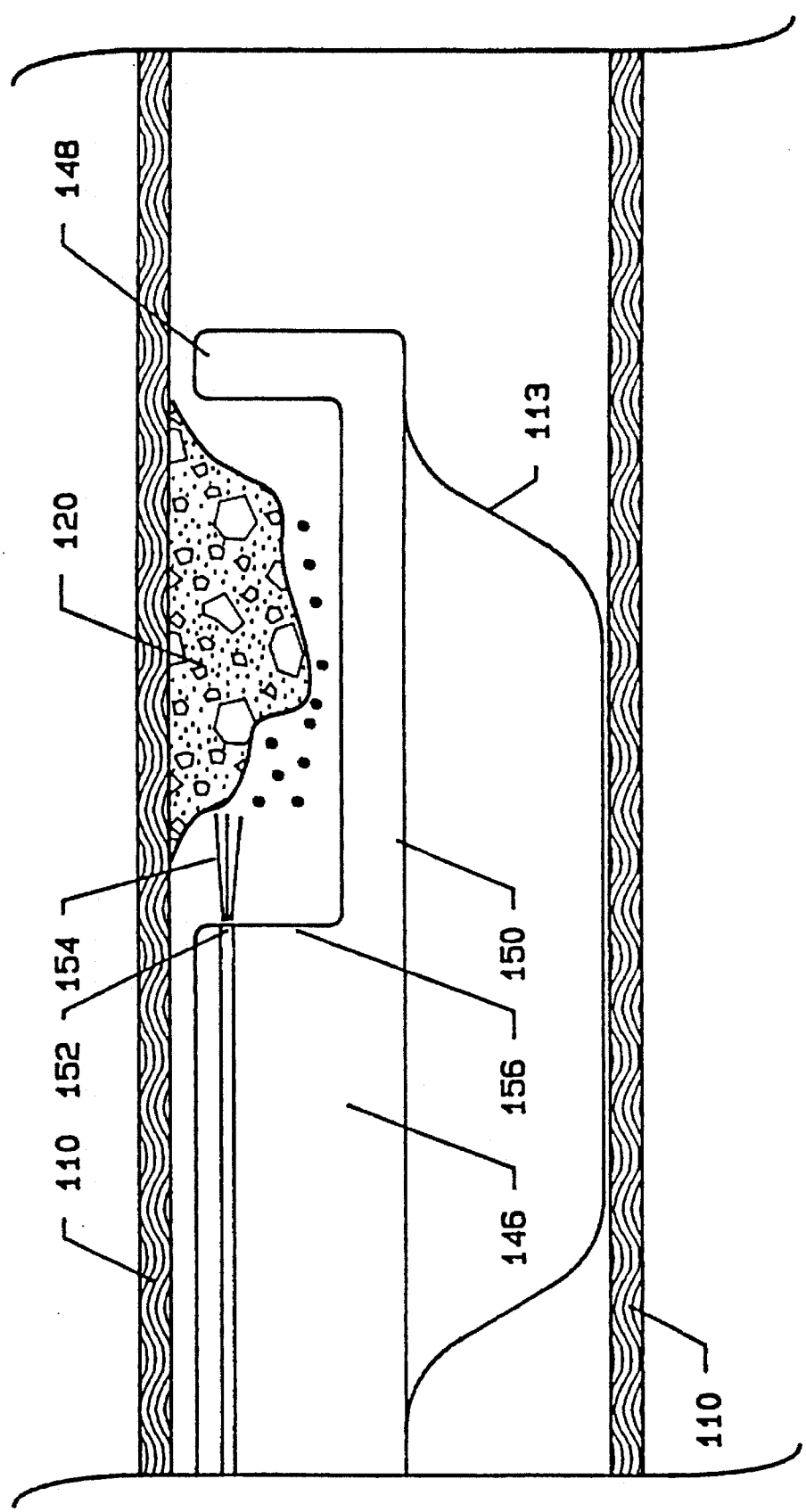
FIG. 3C is a conceptual view of the operation of an atherectomy device having no evacuation lumen.

FIG. 3C is a conceptual view of the operation of another embodiment of an atherectomy catheter. This embodiment is similar to the embodiment of FIG. 3B, except that it has no evacuation lumen. With this approach, deposit 120 is ablated into particles which are sufficiently small as not to cause downstream vessel occlusion prior to removal from the body under normal biochemical processes.

Because no evacuation lumen is present, main catheter body 146 may have a lesser diameter. Wall 156 having high pressure jet 152 yielding high pressure saline stream 154 may be correspondingly smaller. Similarly, narrow portion 150 and target wall 148 may be correspondingly smaller permitting the atherectomy device to be used in smaller vessels. Balloon 113 is inflated and used as previously discussed.

Figure 4:
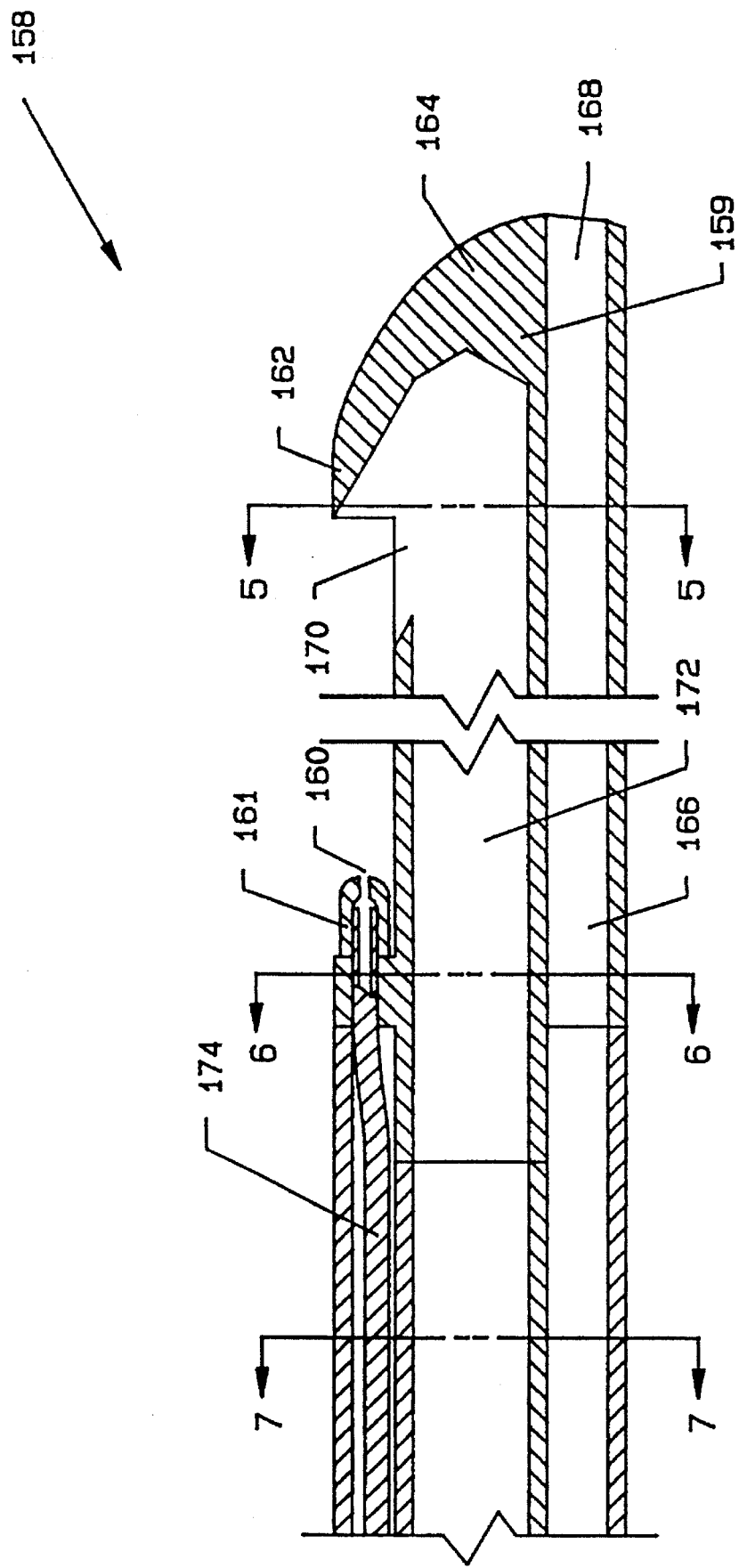
FIG. 4 is a longitudinal sectioned view of the distal end of a catheter employing a first embodiment of the present invention.

FIG. 4 is a longitudinal sectioned view of distal tip 158 of an atherectomy catheter according to the present invention. In this embodiment, a separate guide wire lumen 166 is open at the distal tip 168. This provides for ease in positioning of the atherectomy device as an "over the wire" catheter.

Blunt tip 164 is molded in the shape shown with upper appendage 162 providing the target to protect the arterial wall from direct impingement of a high pressure saline stream.

Hypo tubing 174 is coupled to nozzle assembly 161 having jet orifice 160 of approximately 0.001 inch. In accordance with the present invention, the saline stream emitted from jet orifice 160 will have a pressure of approximately 30,000 psi. The high pressure saline stream from jet orifice 160 is directed distally within the projected span of upper appendage 162 for the safety reasons discussed above. Ablated particulate matter enters evacuation lumen 172 via evacuation port 170. In this embodiment, no ultrasonic transducer array is present.

This particular embodiment of the present invention is configured to operate most efficiently to ablate relatively small, but highly calcified deposits attached to the wall of an artery. It is not well suited to situations involving total occlusions or occlusions which are so complete as to preclude positioning blunt tip 164 and upper appendage 162 distal of the deposit. A distal balloon is not shown in this embodiment although one can be placed in a manner similar to those which follow.

Figure 5:
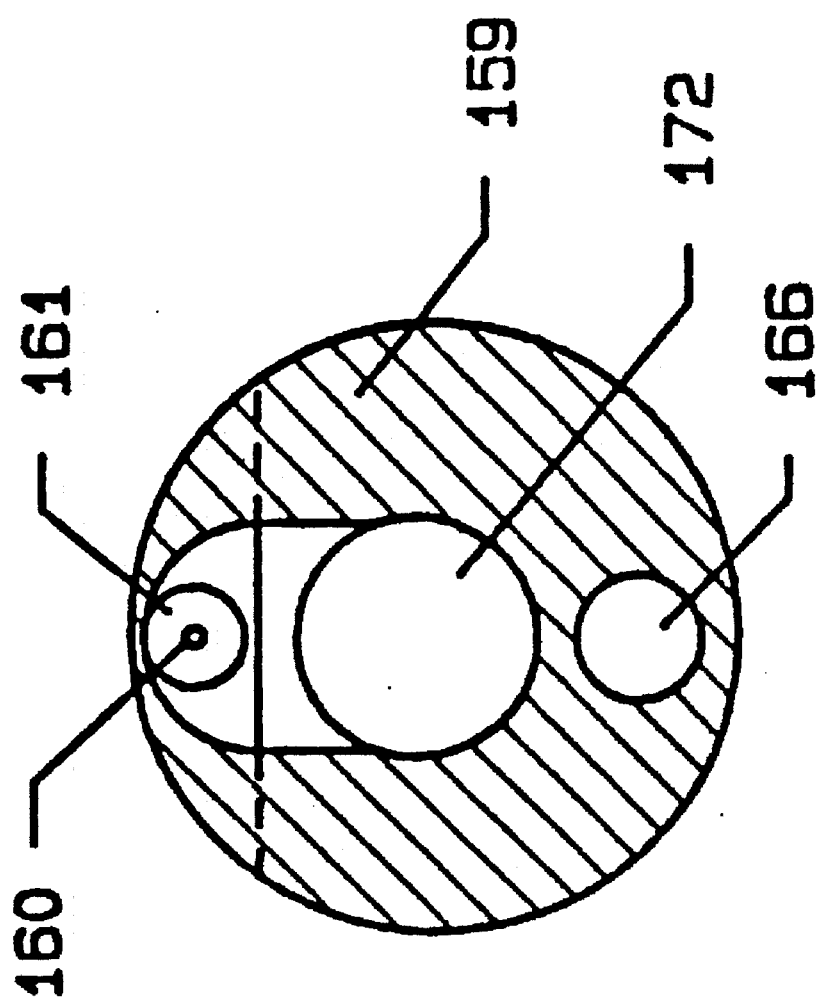
FIG. 5 is a transverse sectioned view of the catheter of FIG. 4.

FIG. 5 is a transverse sectional view of the atherectomy device of FIG. 4. Catheter body 159 has an evacuation lumen 172, a guide wire lumen 166, and nozzle assembly 161.

Figure 6:
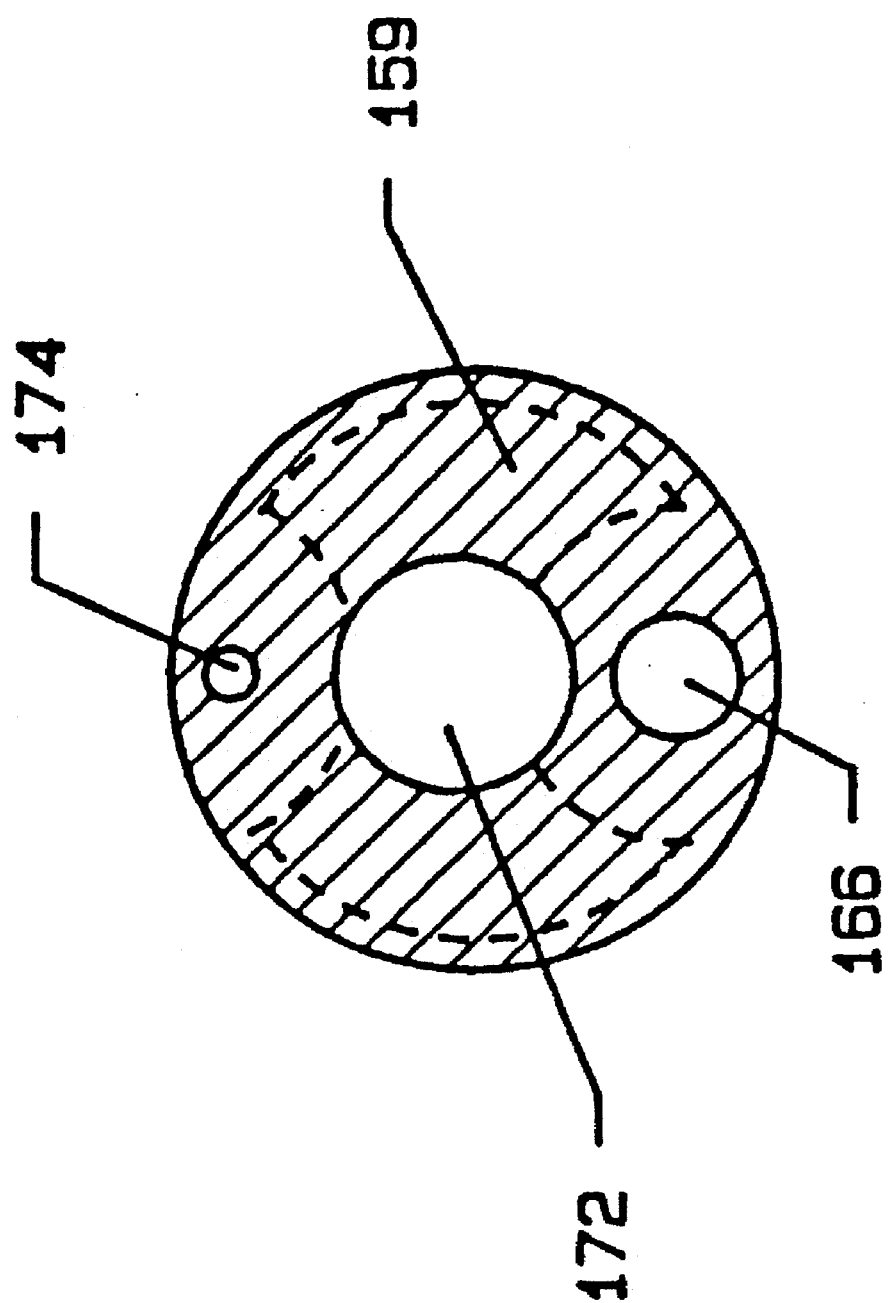
FIG. 6 is a transverse sectioned view of the catheter of FIG. 4.

FIG. 6 is a transverse sectional view of the atherectomy device of FIG. 4 as taken proximal to FIG. 5. All reference components are as previously described.

Figure 7:
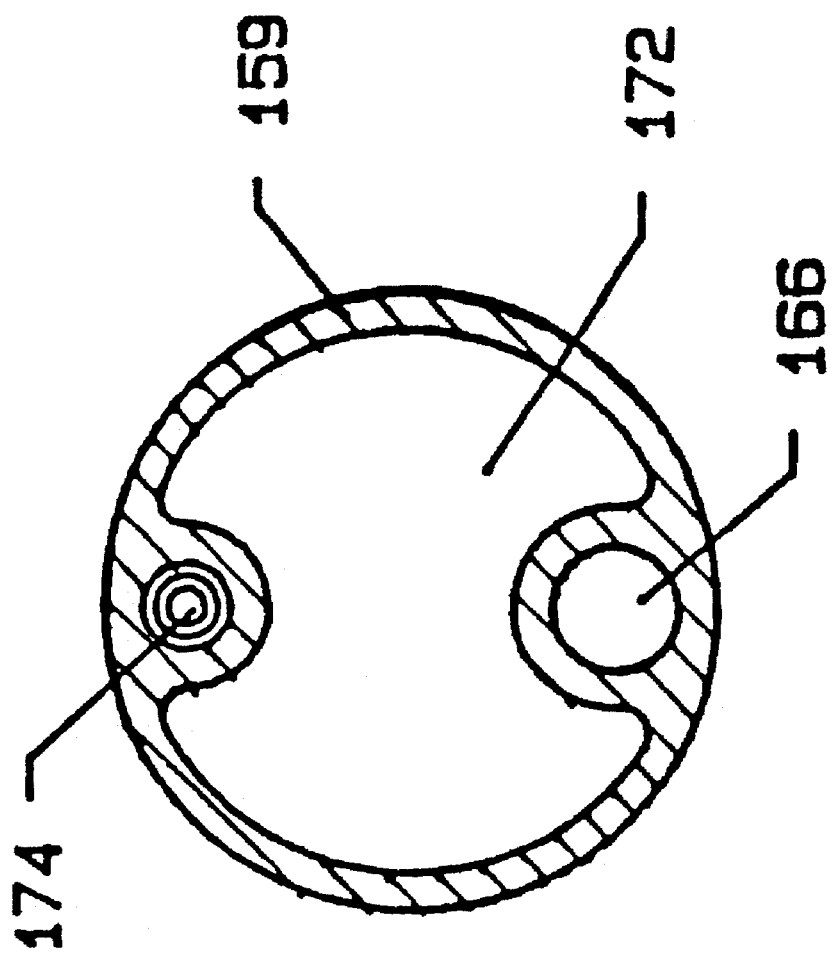
FIG. 7 is a transverse sectioned view of the catheter of FIG. 4.

FIG. 7 is a transverse sectional view of the atherectomy device of FIG. 4 as taken proximal to FIG. 6. Note that for most of its length, catheter body 159 has evacuation lumen 172 as constituting the majority of the cross sectional area. This provides the greatest assurance that evacuation lumen 172 will not clog with particulate matter.

Figure 8:
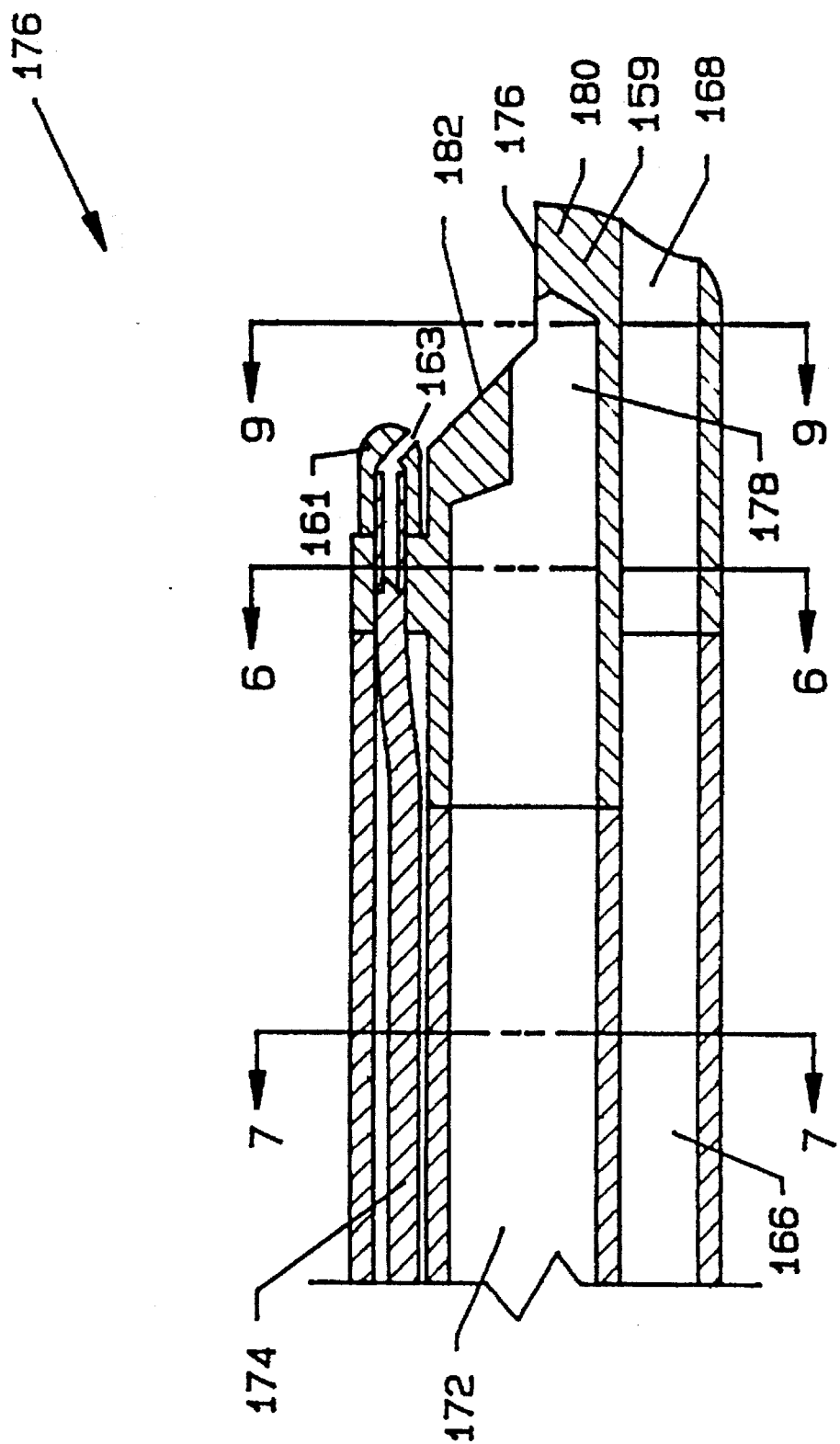
FIG. 8 is a longitudinal sectioned view of the distal end of a catheter employing a second embodiment of the present invention.

FIG. 8 is a longitudinal sectioned view of the distal end 176 of an atherectomy device which is useful for ablating deposits in arteries which have a greater percentage of occlusion. In this configuration, nozzle assembly 161 has a high pressure jet 163 which is angled toward the central longitudinal axis of the catheter. In this way, the effective diameter of the catheter distal to high pressure jet 163 is substantially less than the diameter proximal to that point. The result is that the high pressure saline stream tends to cut away at the proximal surface of the deposit rather than longitudinally as with the embodiment of FIG. 4.

As with the other embodiments, high pressure jet 63 is directed toward distal end 176 as a safety measure. The distal tip is truncated along slope 182 to provide space for positioning the deposit. Distal end 180, though much smaller in this embodiment, must yet be rounded to prevent trauma. A distal balloon is not shown in this embodiment. One can be added to hold the catheter preferentially against one side of the vessel. The device can also function without a balloon to follow a wire across a lesion and enlarge the opening.

Figure 9:
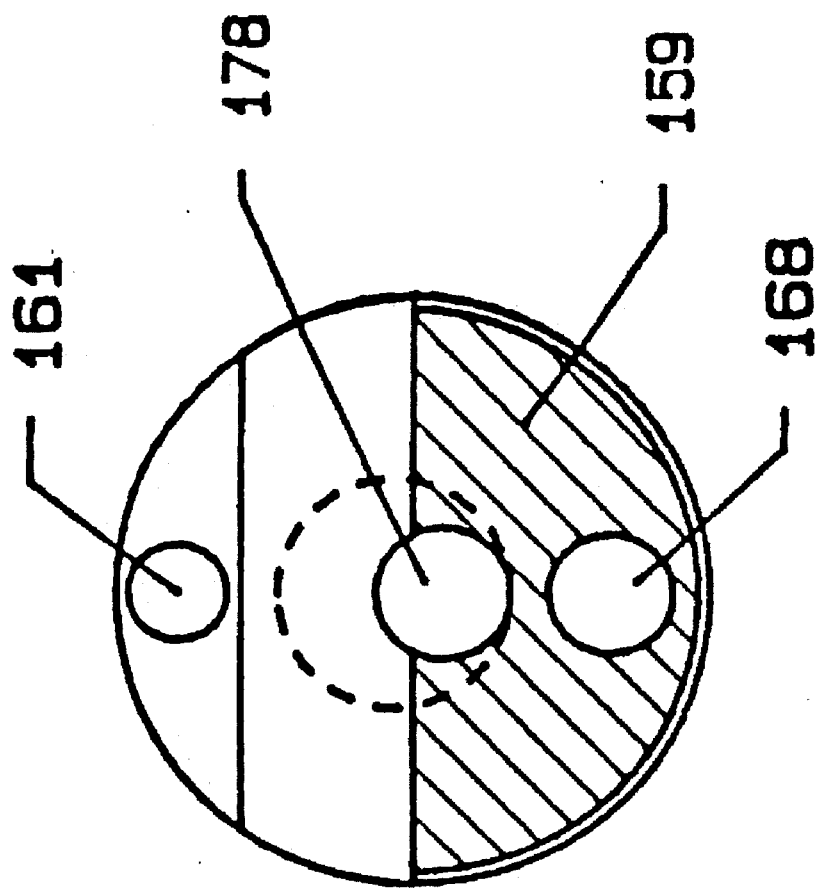
FIG. 9 is a transverse sectioned view of the catheter of FIG. 8.

FIG. 9 is a transverse sectioned view of the atherectomy device of FIG. 8. Evacuation port 178 is entered at an angle by the particulate matter to be removed (see also FIG. 8). All other referenced elements are as previously described.

Figure 10:
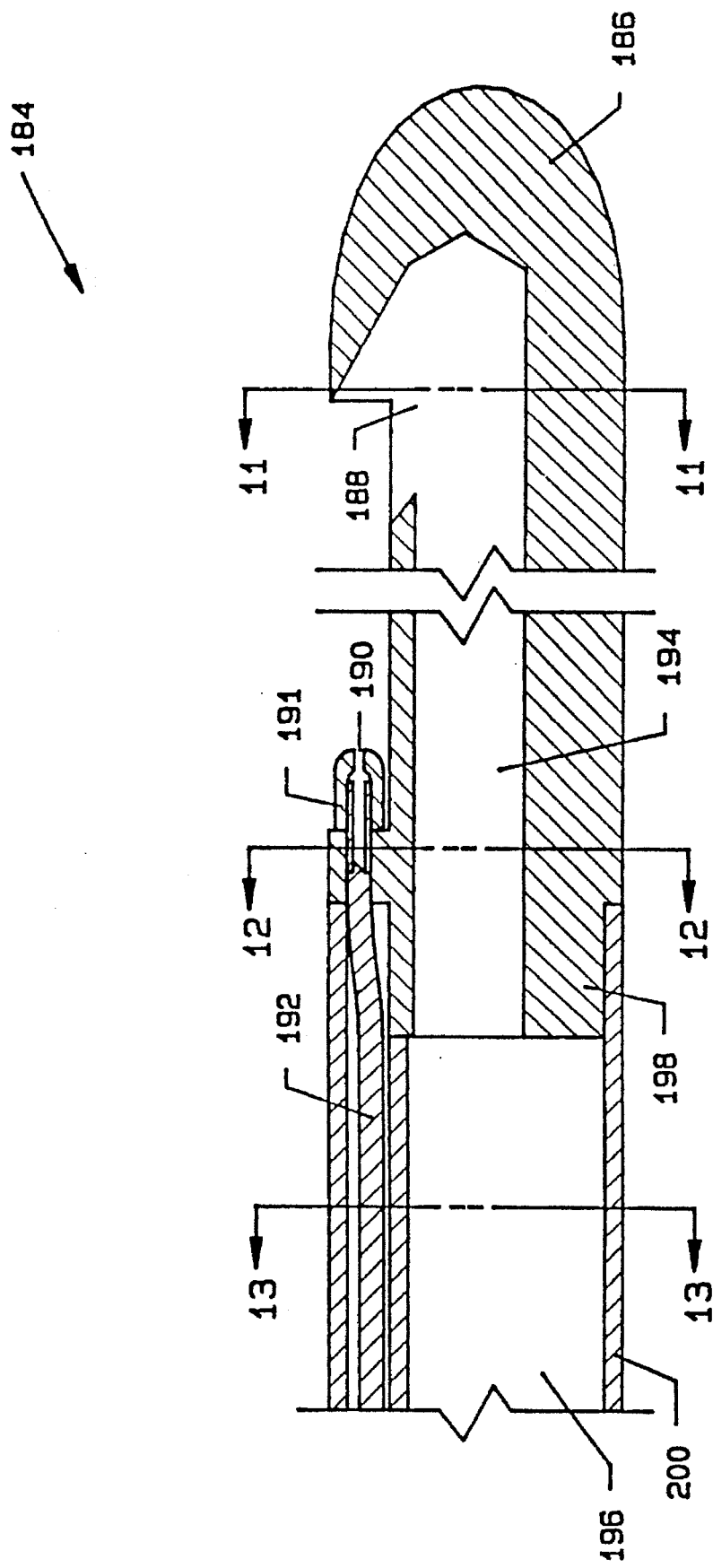
FIG. 10 is a longitudinal sectioned view of the distal end of a catheter employing a third embodiment of the present invention.

FIG. 10 is a longitudinal sectioned view of the distal end 184 of an atherectomy device without guide wire lumen. Positioning of this device at the site of the deposit must be performed without the aid of a guide wire. Oftentimes a guide catheter is used with such devices.

Catheter body 200 is extruded in the standard fashion. Distal tip 186 is then affixed at 198 with adhesive, heat sealing, or other suitable attachment technique. Evacuation port 188 and tip evacuation lumen 194 are molded into distal tip 186 in the positions shown and are connected to the evacuation lumen 196. Hypo tubing 192 is attached to nozzle assembly 191 containing high pressure jet 190 as previously described.

This particular embodiment performs much in the same fashion as the embodiment of FIG. 4. The major difference is that this embodiment does not have a guide wire lumen.

This catheter is shown without a balloon, although one can be added to the side opposite the jet. The balloon holds the catheter against the deposit on one side of the vessel wall.

Figure 11:
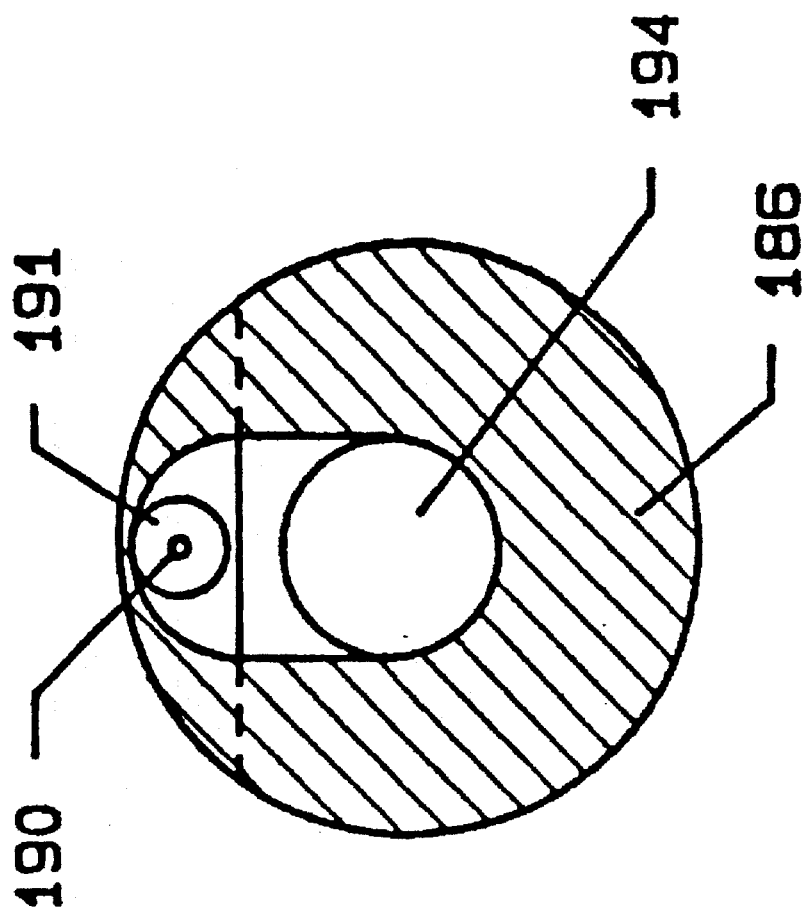
FIG. 11 is a transverse sectioned view of the catheter of FIG. 10.

FIG. 11 is a transverse sectioned view of the catheter of FIG. 10. All referenced elements are as previously described.

Figure 12:
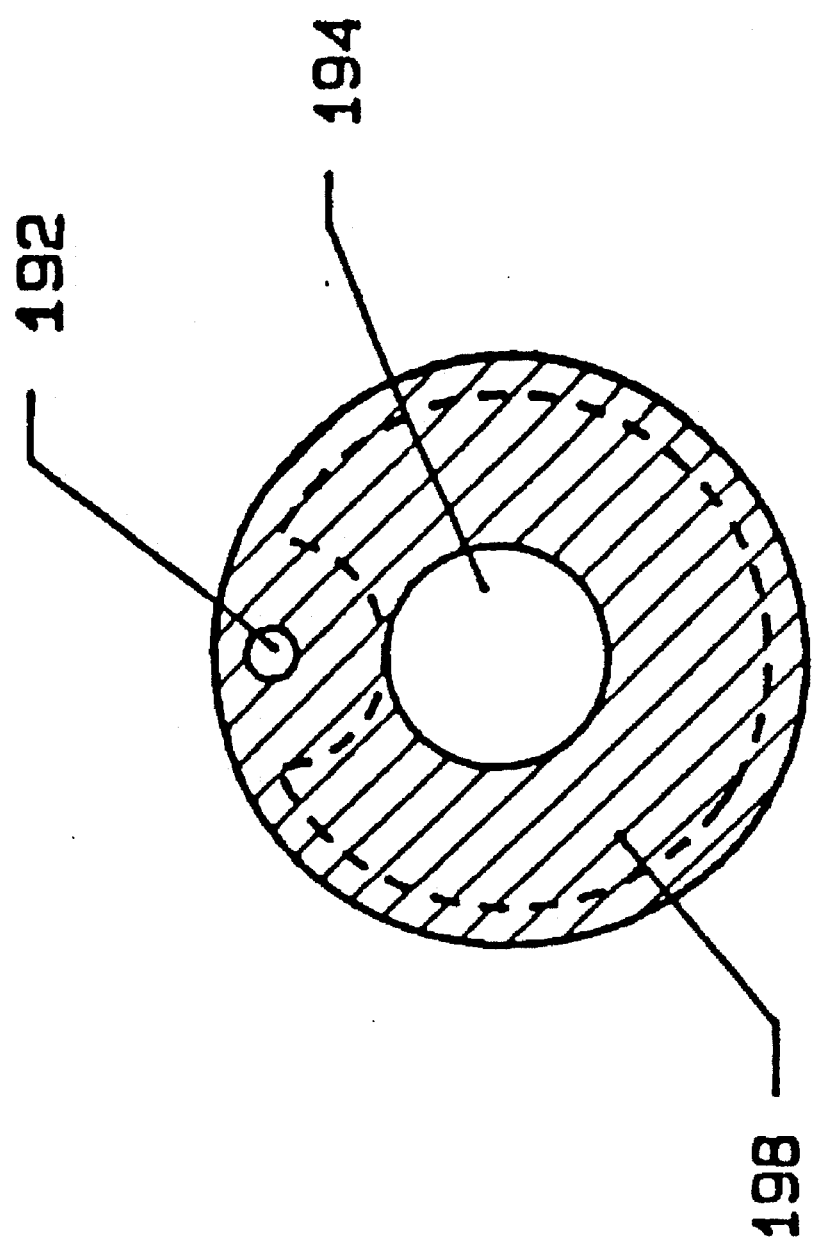
FIG. 12 is a transverse sectioned view of the catheter of FIG. 10.

FIG. 12 is a transverse sectioned view of the catheter of FIG. 10 taken proximal of FIG. 11. All referenced elements are as previously described.

Figure 13:
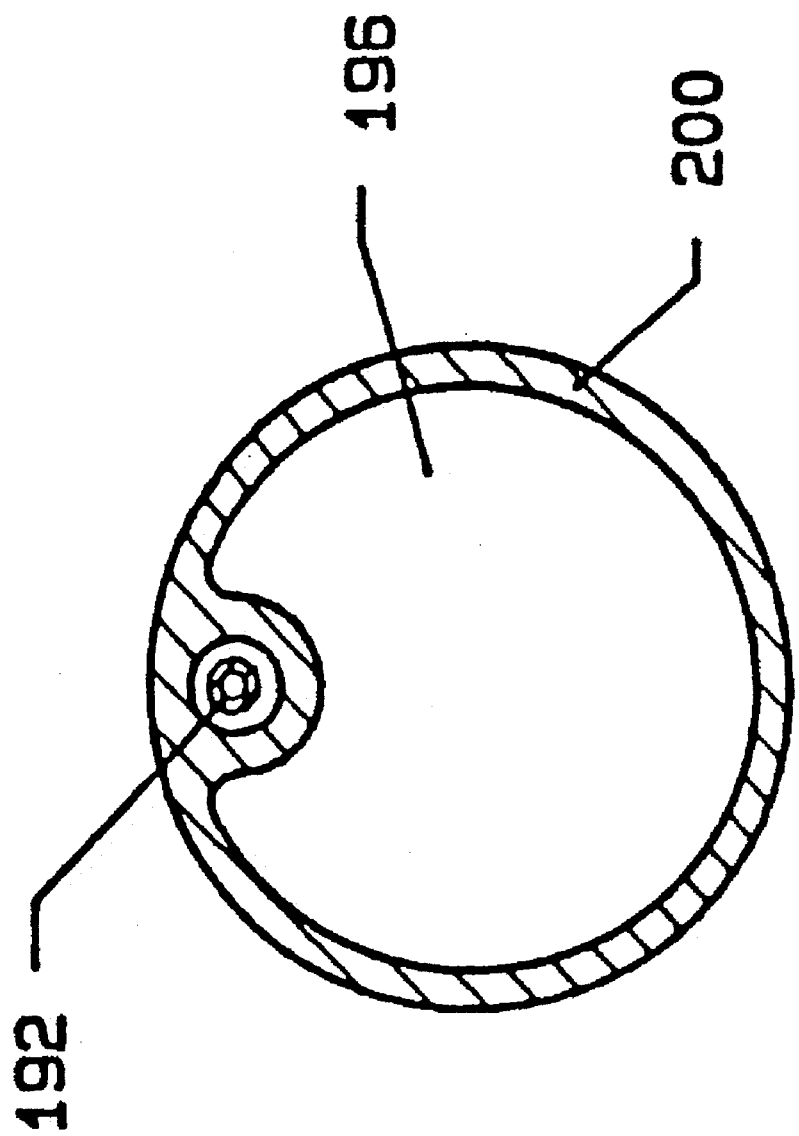
FIG. 13 is a transverse sectioned view of the catheter of FIG. 10.

FIG. 13 is a transverse sectioned view of the catheter of FIG. 10 taken proximal to distal tip 186. As can be seen with previous embodiments, evacuation lumen 196 occupies most of the cross sectional area of the main catheter body.

Figure 14:
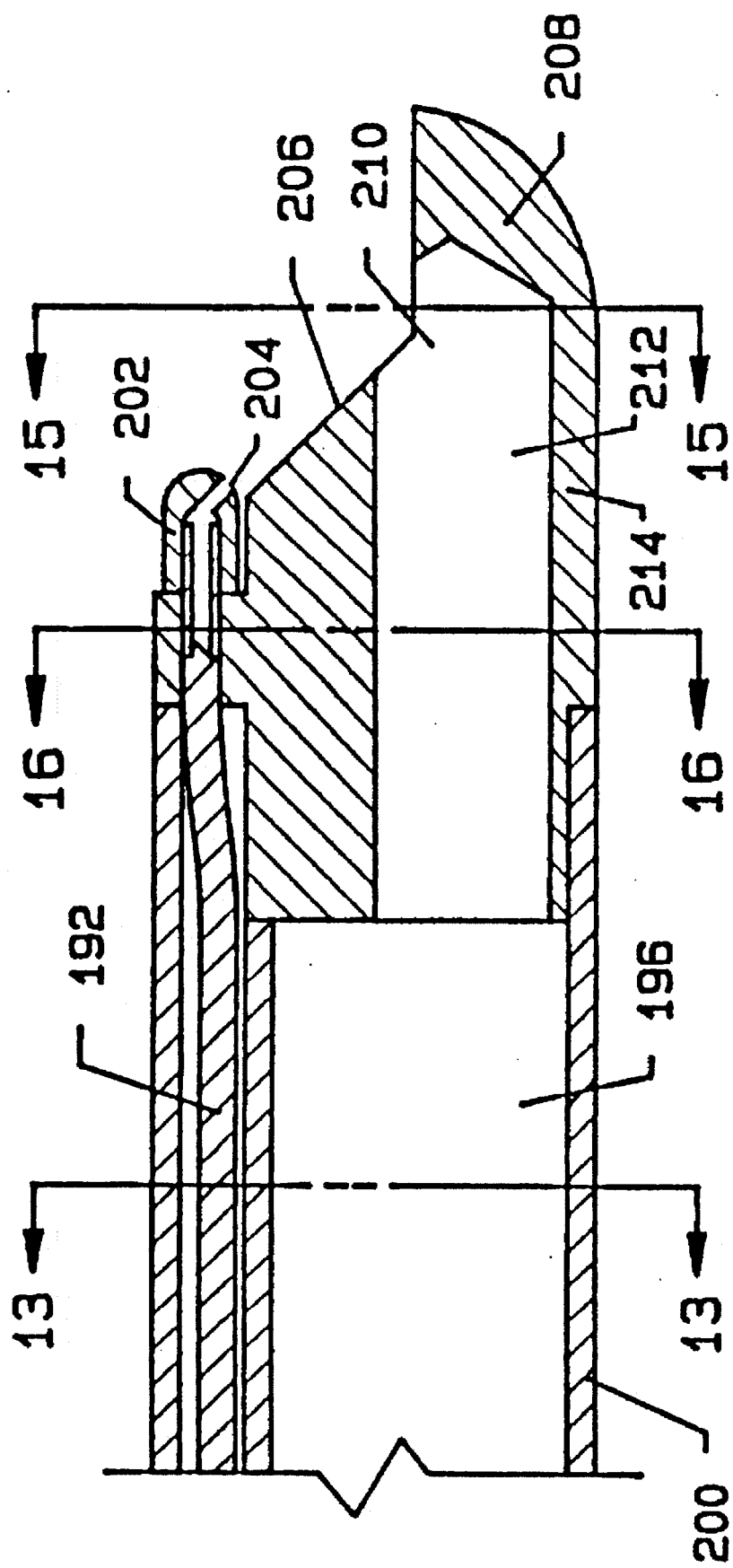
FIG. 14 is a longitudinal sectioned view of the distal end of a catheter employing a fourth embodiment of the present invention.

FIG. 14 is a longitudinal sectioned view of the distal end of an alternative embodiment of an atherectomy device similar to the embodiment of FIG. 8, except that it has no guide wire lumen, where all numerals correspond to those elements previously described. Distal tip 208 is molded having extension 214, evacuation port 210, tip evacuation lumen 212 and slope 206. High pressure jet 204 of nozzle assembly 202 is angled toward the central longitudinal axis as in the embodiment of FIG. 8. Again this tends to ablate the deposit from the proximal surface rather than longitudinally. A distal balloon (not shown) may be added as appropriate.

Figure 15:
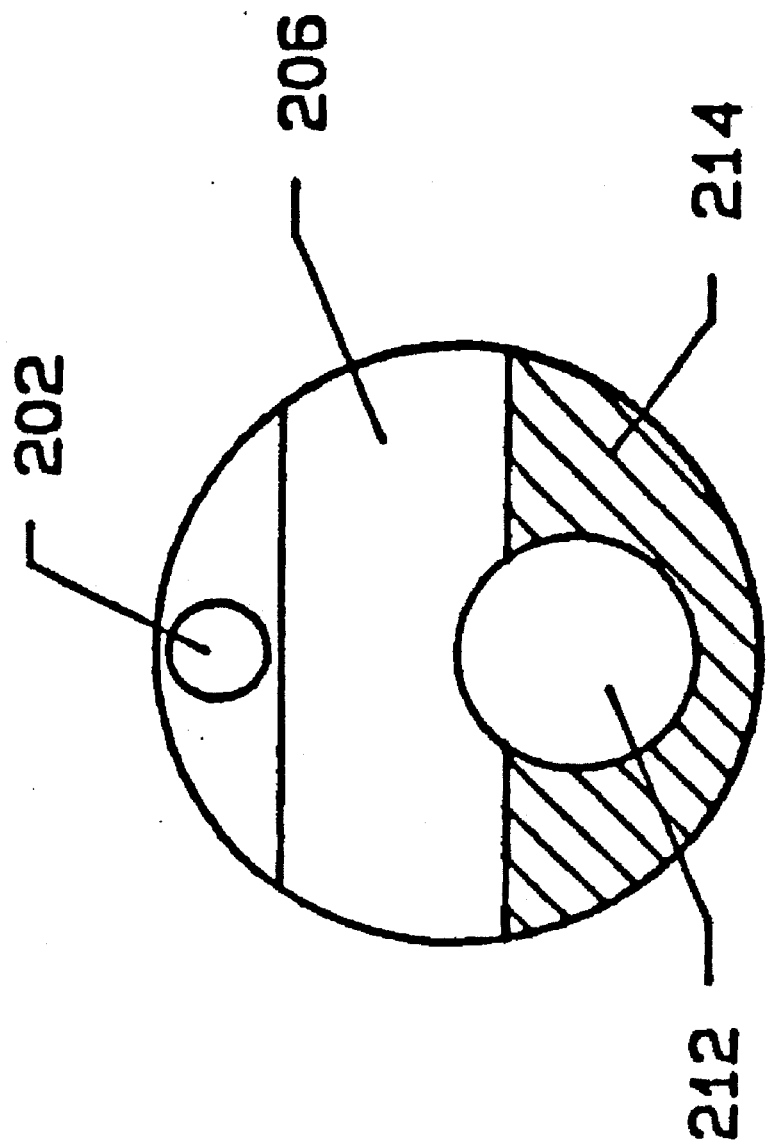
FIG. 15 is a transverse sectioned view of the catheter of FIG. 14.

FIG. 15 is a transverse sectioned view of the atherectomy device of FIG. 14. All referenced elements are as previously described.

Figure 16:
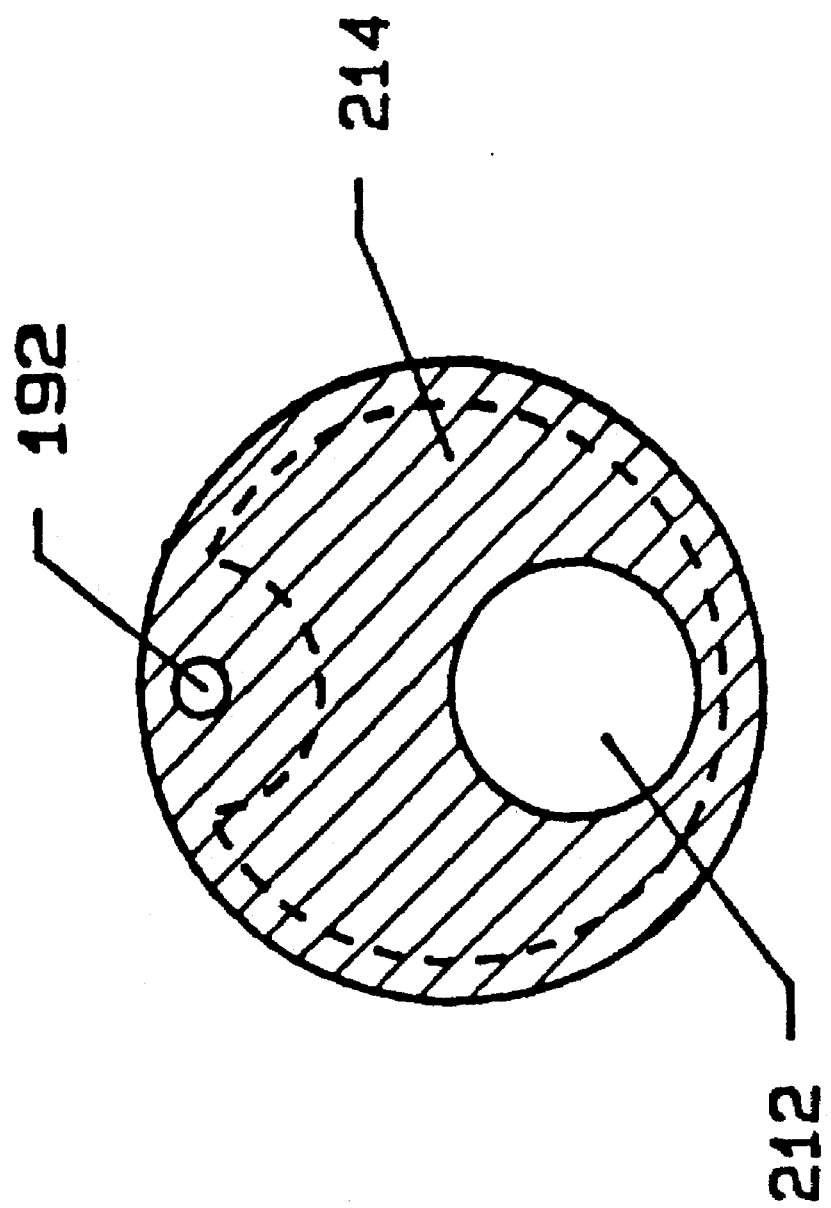
FIG. 16 is a transverse sectioned view of the catheter of FIG. 14.

FIG. 16 is a transverse sectioned view of the atherectomy device of FIG. 14 taken proximal to FIG. 15. All referenced elements are as previously described.

Figure 17:
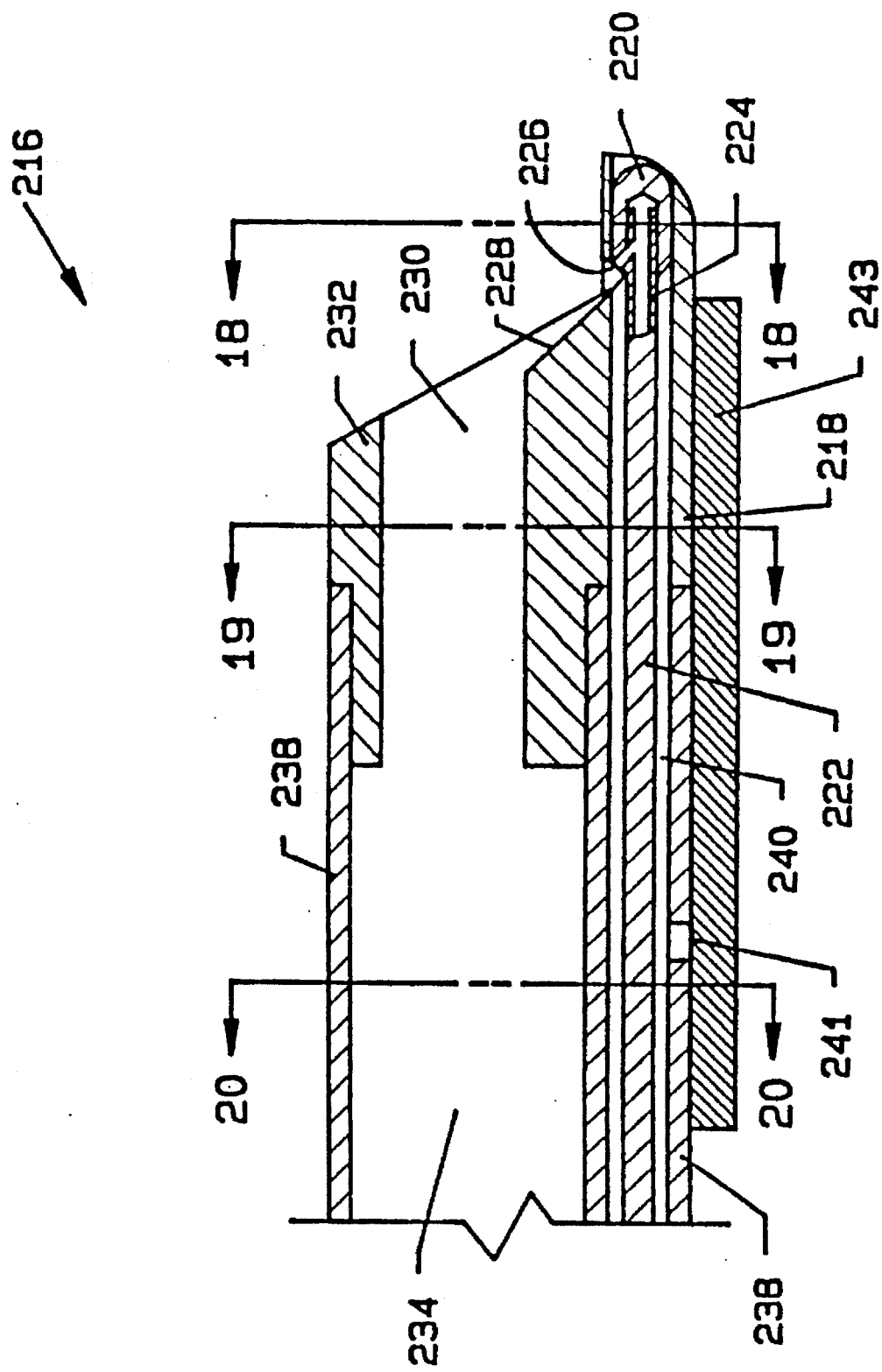
FIG. 17 is a longitudinal sectioned view of the distal end of a catheter employing a fifth embodiment of the present invention.

FIG. 17 is a longitudinal view of the distal end of an atherectomy device 216 employing an alternative embodiment of the present invention. In this embodiment, hypo tubing 222 runs the length of lumen 240 of catheter body 238 to distal tip 220 where it is attached to nozzle assembly 224. In this way, hypo tubing 222 has no sharp bends near the distal end of the catheter. Lumen 240 is coupled to balloon inflation port 241 which is used to inflate balloon 243. The balloon is used to hold the catheter against the deposit on the vessel wall. The catheter may also be made without the balloon.

High pressure jet 226 of nozzle assembly 224 is angled toward the central longitudinal axis of the catheter. This permits the atherectomy device to be applied to deposits which are near to totally occluding the vessel, because the effective diameter of the device distal to the deposit comprises only the diameter of distal tip 220. End member 218 is formed to provide slope 228 and slope 232 ensuring that the high pressure saline stream from high pressure jet 226 will impinge upon the deposit to be ablated. Evacuation port 230 is open permitting the particulate matter to enter evacuation lumen 234.

As with the other embodiments wherein the high pressure jet is angled toward the central longitudinal axis, the present embodiment ablates the deposit along the proximal surface rather than longitudinally. Again, this makes the device most applicable to deposits which occupy a large fraction of the cross sectional area of the vessel lumen.

Figure 18:
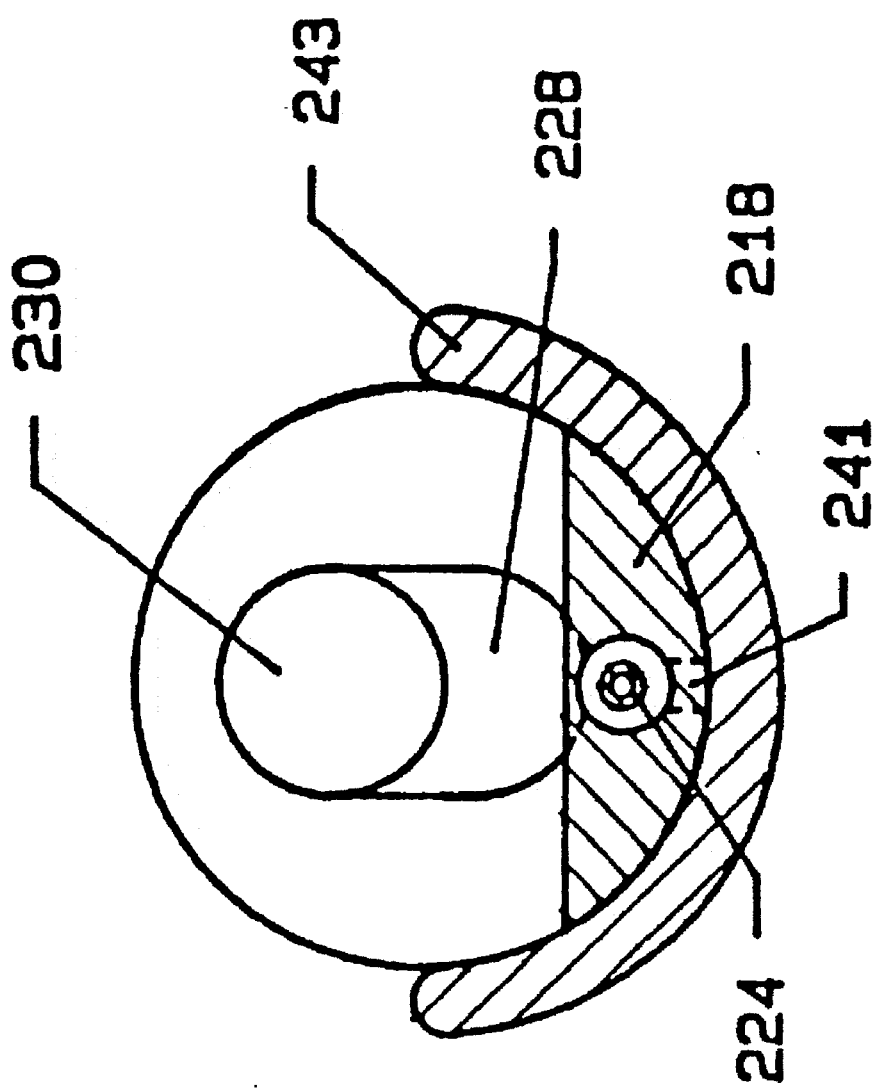
FIG. 18 is a transverse sectioned view of the catheter of FIG. 17.

FIG. 18 is a transverse sectional view of the embodiment of FIG. 17 taken from the distal end of the atherectomy device. All referenced elements are as previously described.

Figure 19:
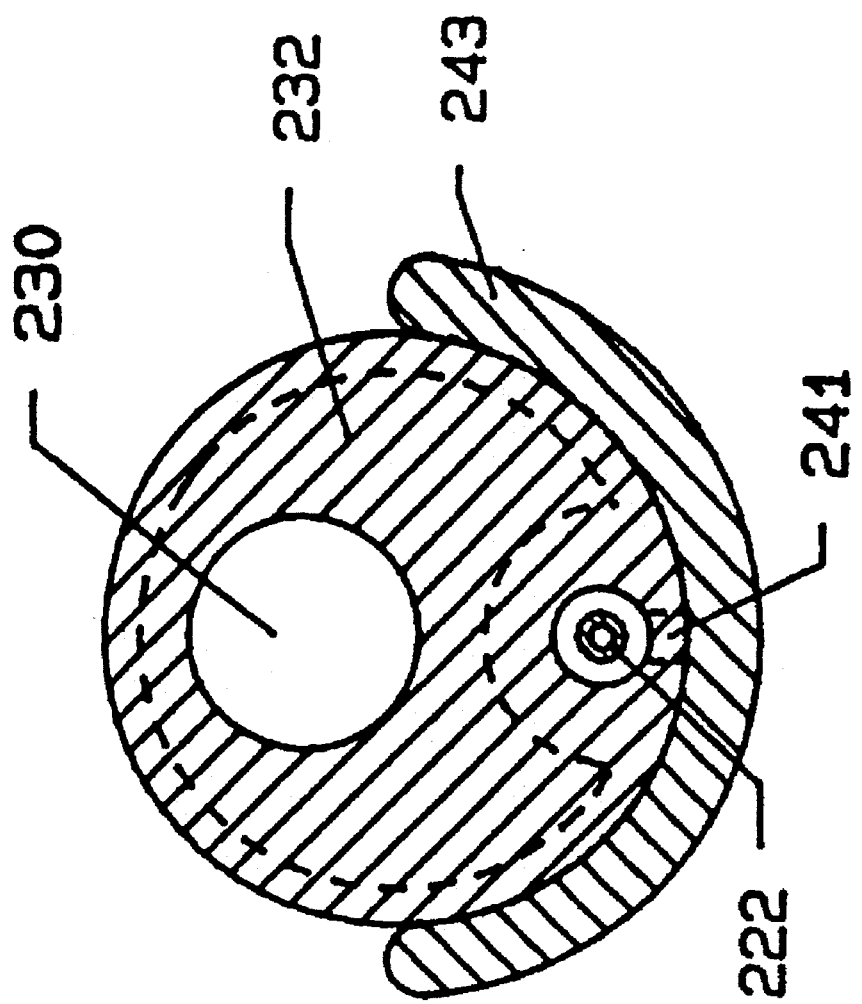
FIG. 19 is a transverse sectioned view of the catheter of FIG. 17.

FIG. 19 is a transverse sectional view of the embodiment of FIG. 17 taken proximal to FIG. 18. All referenced elements are as previously described.

Figure 20:
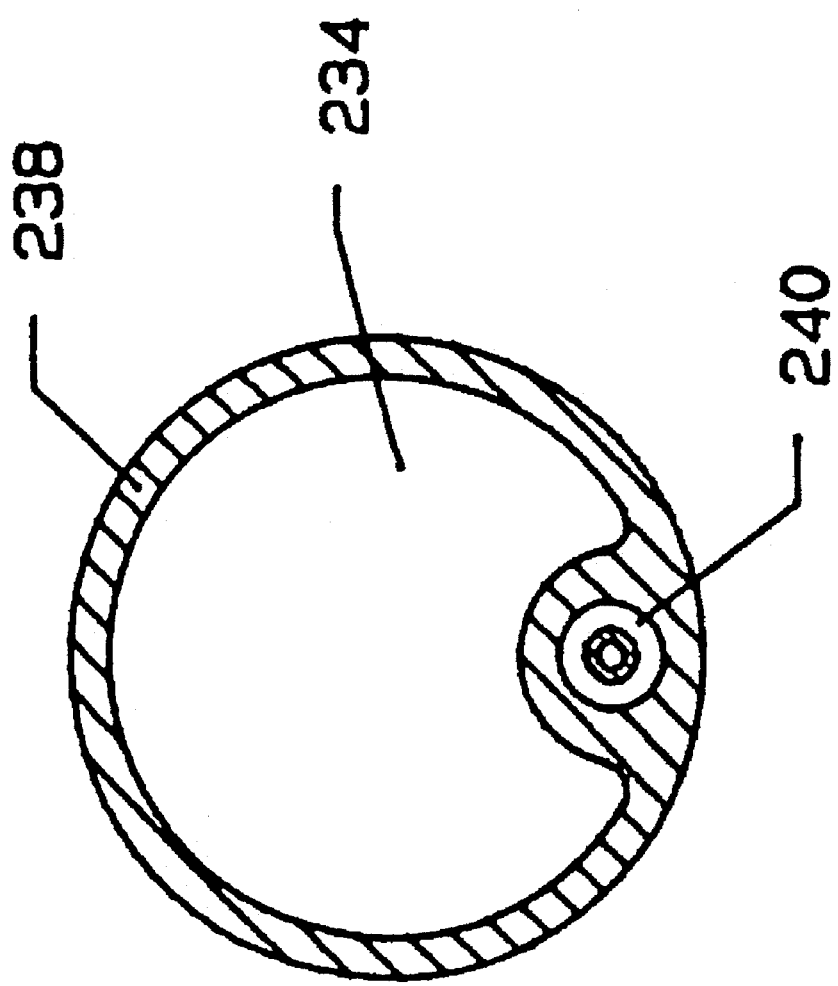
FIG. 20 is a transverse sectioned view of the catheter of FIG. 17.

FIG. 20 is a transverse sectional view of the embodiment of FIG. 17 taken proximal of end member 218. Evacuation lumen 234 occupies the majority of the cross sectional area of the main catheter body.

Figure 21:
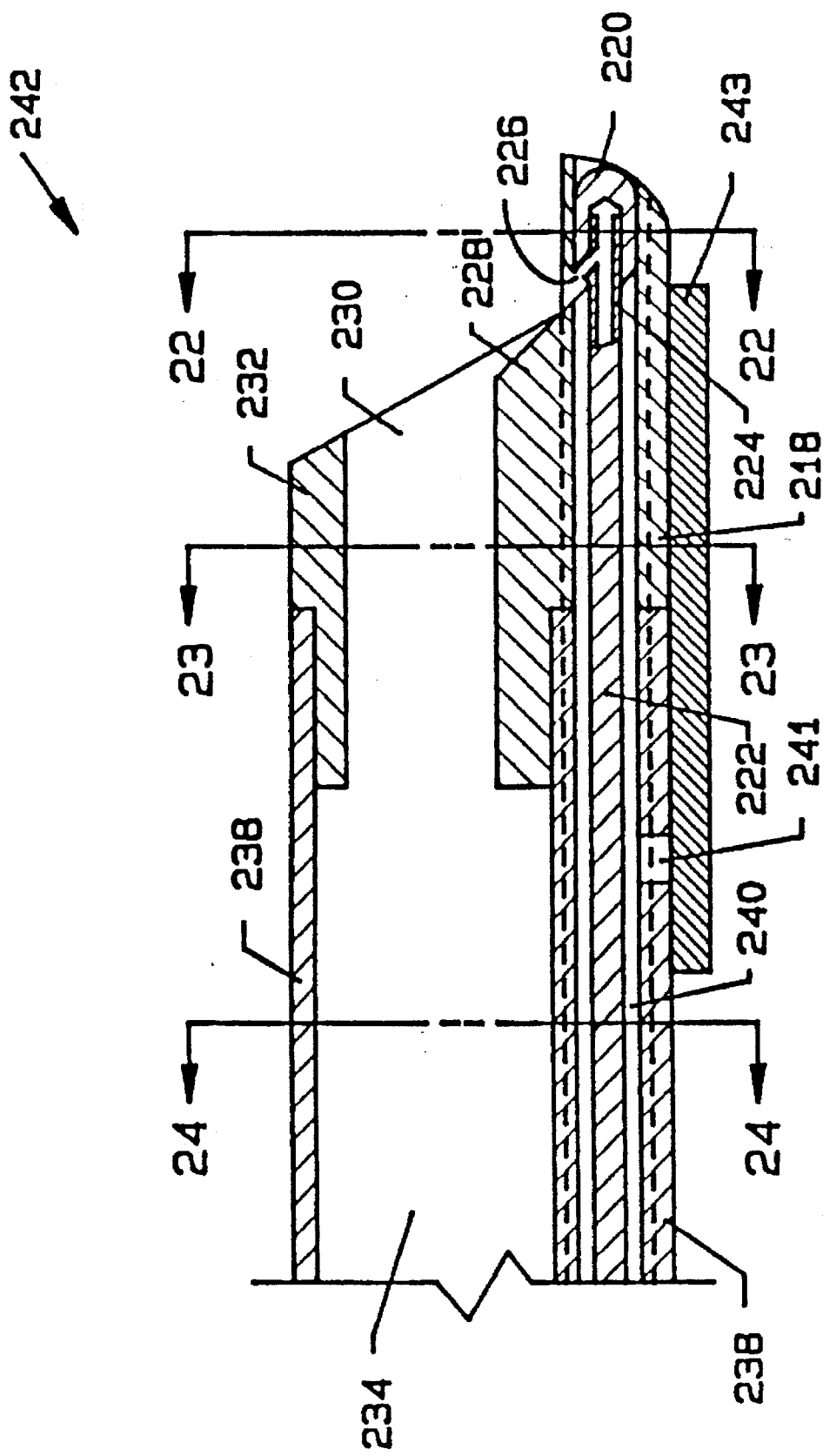
FIG. 21 is a longitudinal sectioned view of the distal end of a catheter employing a sixth embodiment of the present invention.

FIG. 21 is a longitudinal sectioned view of an atherectomy device 242 similar to the embodiment of FIG. 17, except that it has a guide wire lumen 244. All other referenced elements are as previously described. Balloon 243 is used to push the catheter against the deposit on the vessel wall. The catheter can also function without the balloon.

Figure 22:
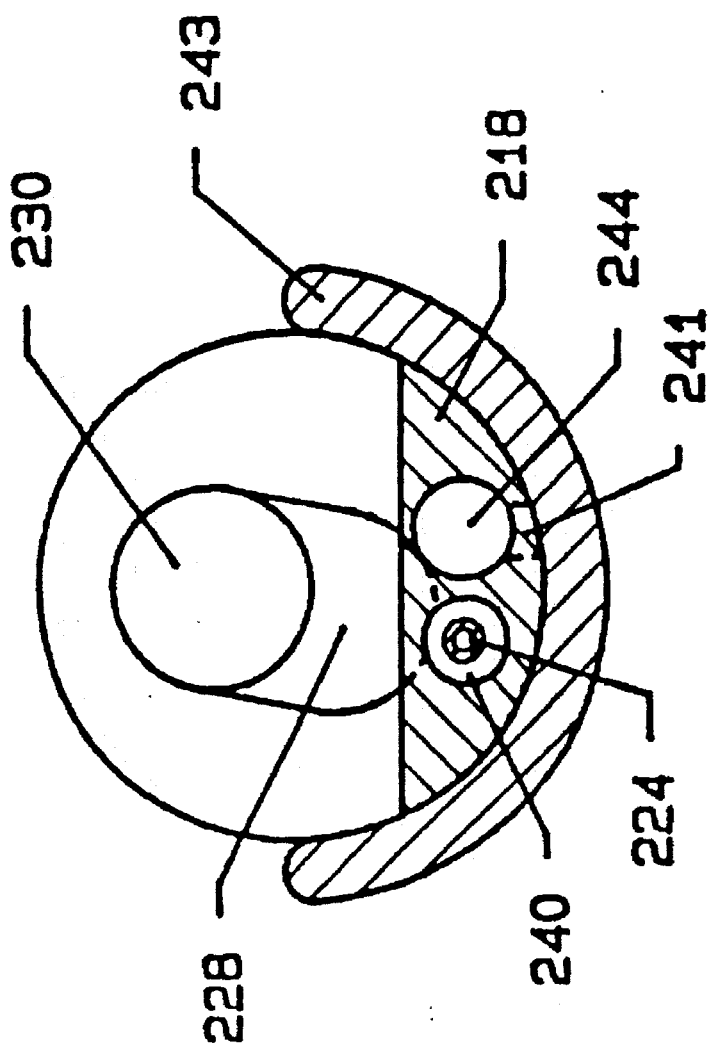
FIG. 22 is a transverse sectioned view of the catheter of FIG. 21.

FIG. 22 is a transverse sectioned view of atherectomy device 242. It is similar to atherectomy device 216, except that it has a guide wire lumen 244. To accommodate guide wire lumen 244 with the smallest increase in distal cross sectional area, guide wire lumen 244 is located off center with respect to nozzle assembly 224.

Figure 23:
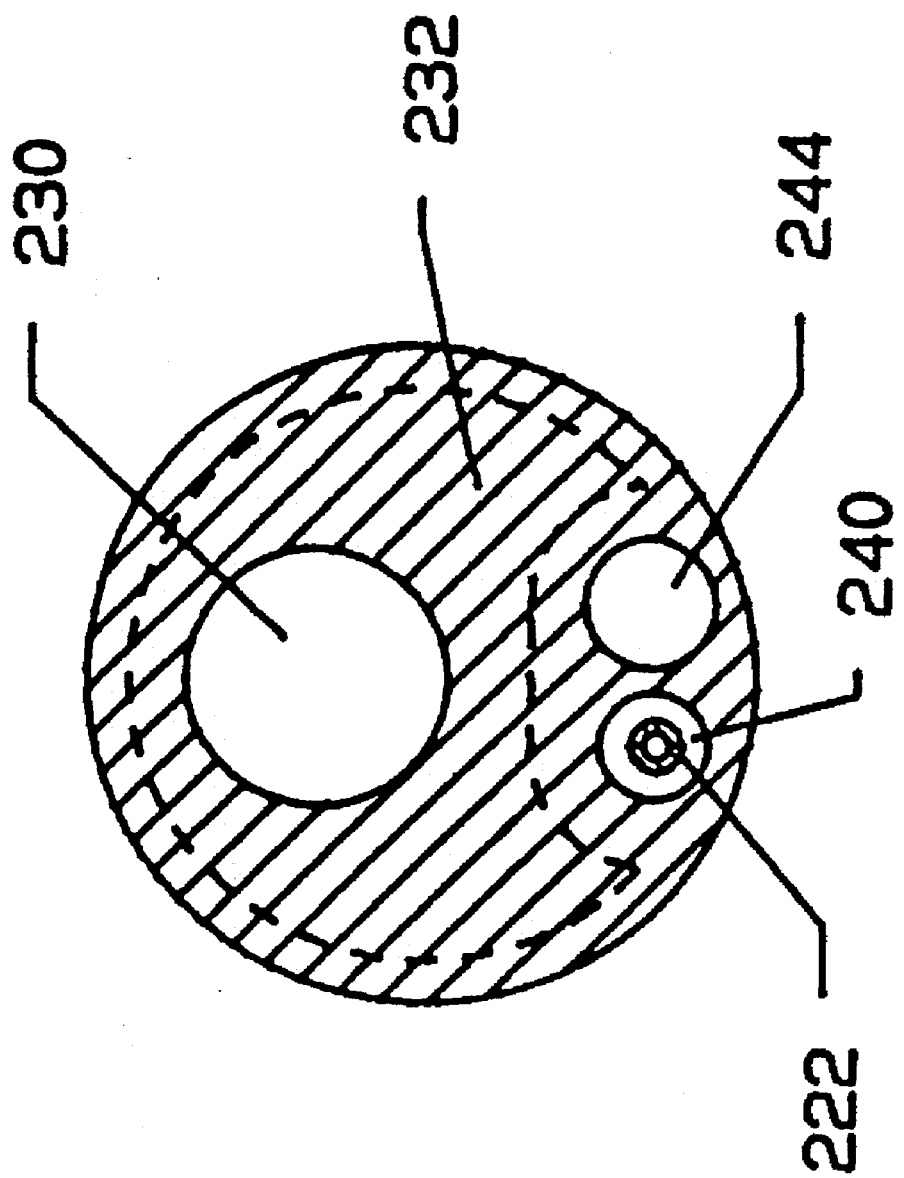
FIG. 23 is a transverse sectioned view of the catheter of FIG. 21.

FIG. 23 is a transverse sectioned view of atherectomy device 242 taken proximal to FIG. 22. Guide wire lumen 244 has a larger diameter than hypo tubing 222.

Figure 24:
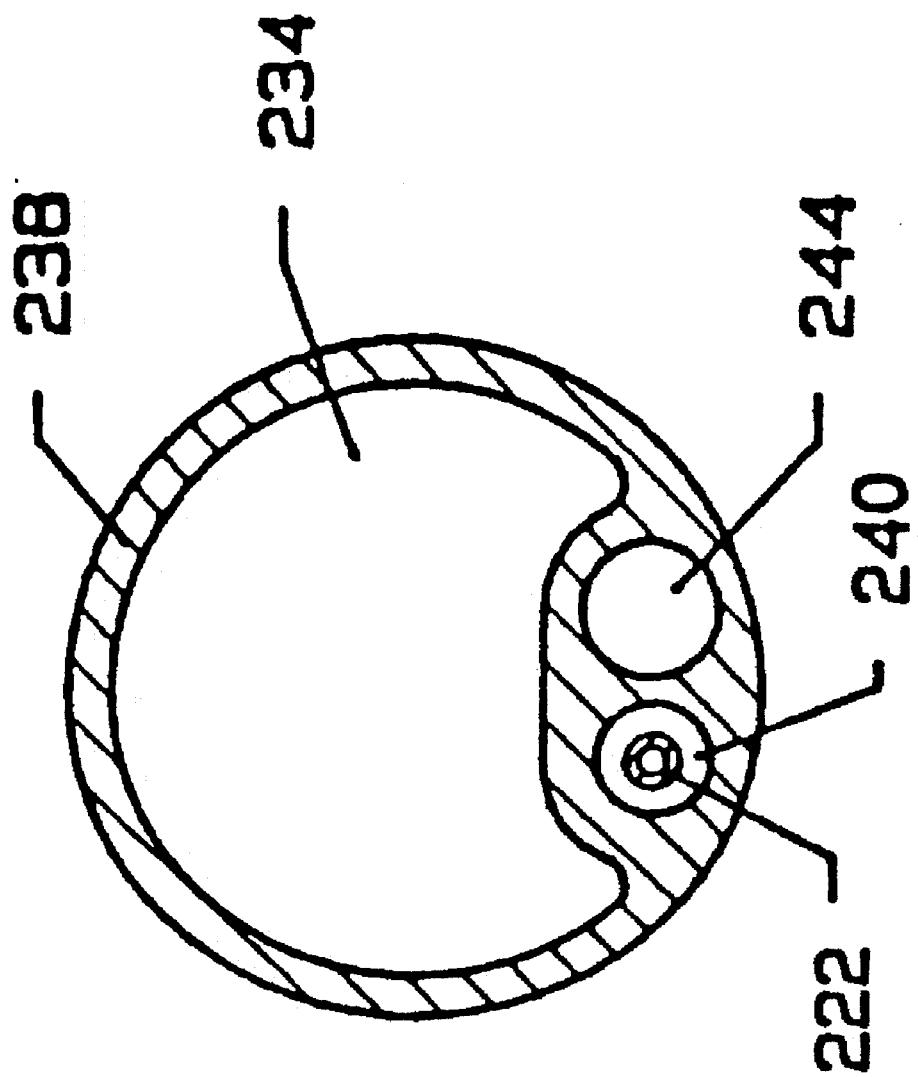
FIG. 24 is a transverse sectioned view of the catheter of FIG. 21.

FIG. 24 is a transverse sectioned view of atherectomy device 242 taken proximal to end member 218. Evacuation lumen 234 is by far the largest of the three lumens. Lumen 240, which accommodates hypo tubing 222, is the smallest lumen.

Figure 25:
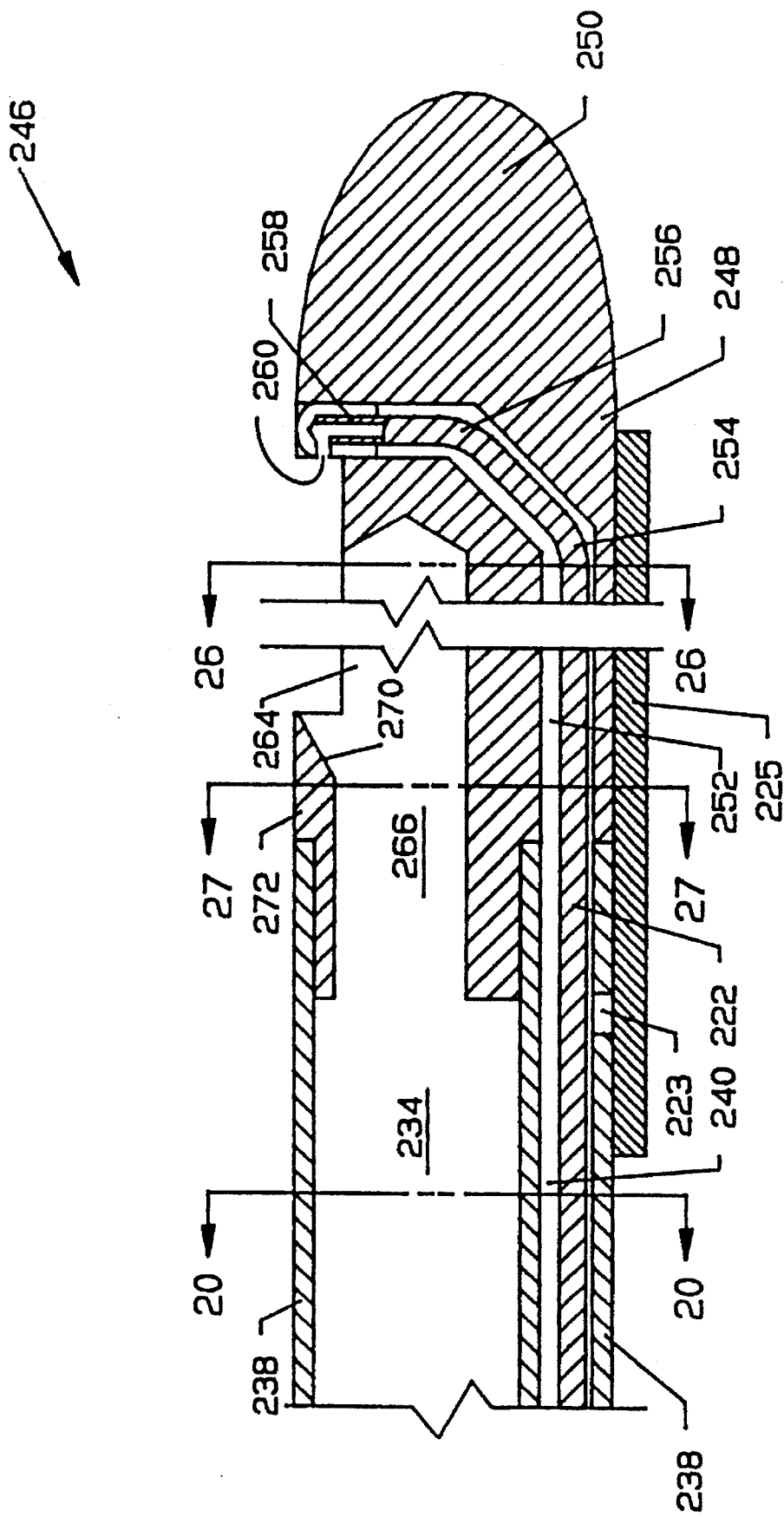
FIG. 25 is a longitudinal sectioned view of the distal end of a catheter employing a seventh embodiment of the present invention.

FIG. 25 is a longitudinal sectioned view of an atherectomy device 246 employing another embodiment of the present invention where all numerals correspond to those elements previously described. In this embodiment, high pressure saline transfers through hypo tubing 222 having bends at point 254 and point 256. Nozzle assembly 258 has a high pressure jet 260 directed proximally. Lumen 240 of catheter body 238 couples to lumen 252, which accommodates hypo tubing 222 and is coupled to balloon inflation port 223 which is used to inflate balloon 225. Distal tip 250 of end member 248 is smoothly rounded to reduce trauma.

End member 248 is molded with surface 272 and slope 270 defining evacuation port 264. Tip evacuation lumen 266 couples to evacuation lumen 234 of catheter body 238. Surface 272 of end member 248 serves as an axial continuation of the outer surface of catheter body 238.

Atherectomy device 246 tends to supply a highly controlled high pressure saline stream at a precise delivery point. As such, it is most applicable to those applications having minimal occlusion by a very hard deposit lying very close to the vessel wall. This approach is also appropriate to complete the ablation of a deposit which is partially ablated using a different embodiment.

Figure 26:
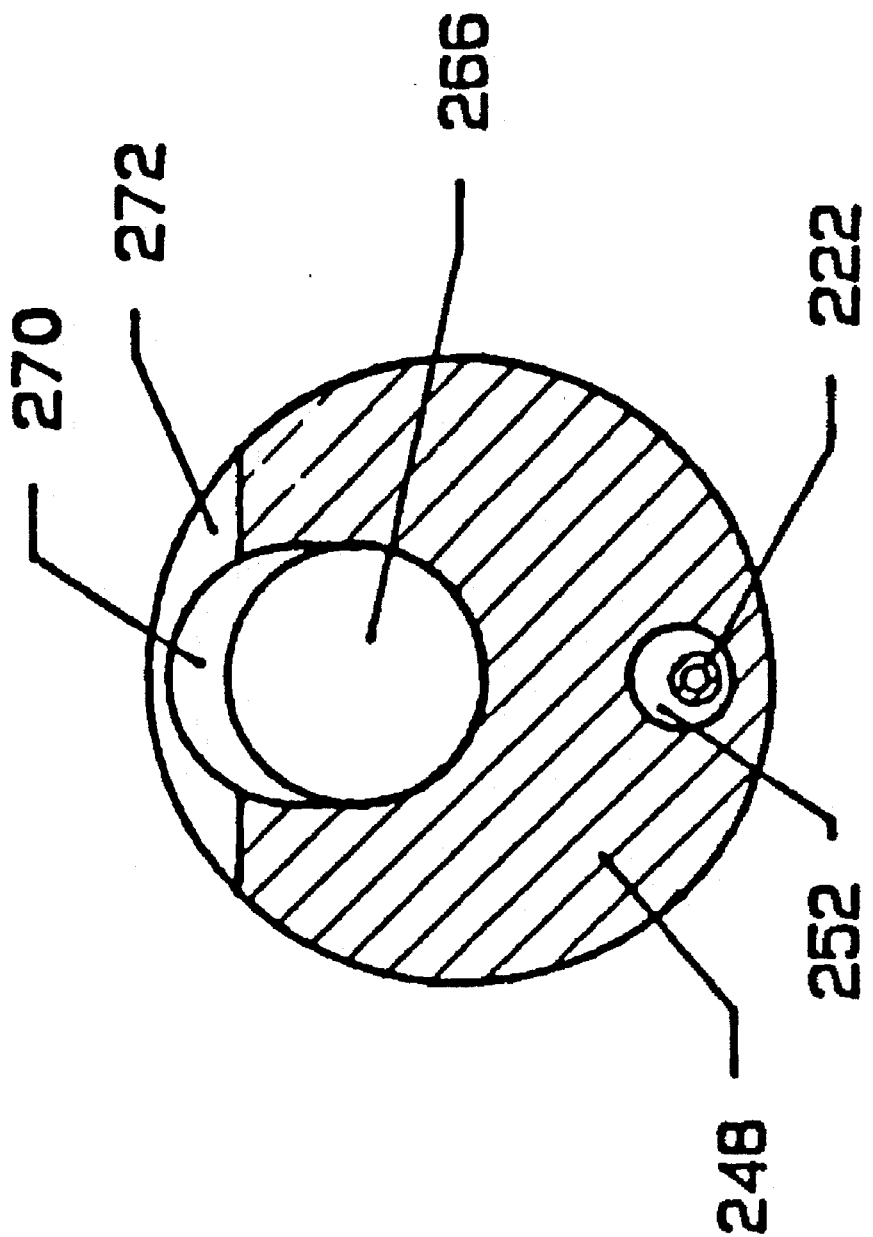
FIG. 26 is a transverse sectioned view of the catheter of FIG. 25.

FIG. 26 is a transverse sectioned view of atherectomy device 246. All referenced elements are as previously described.

Figure 27:
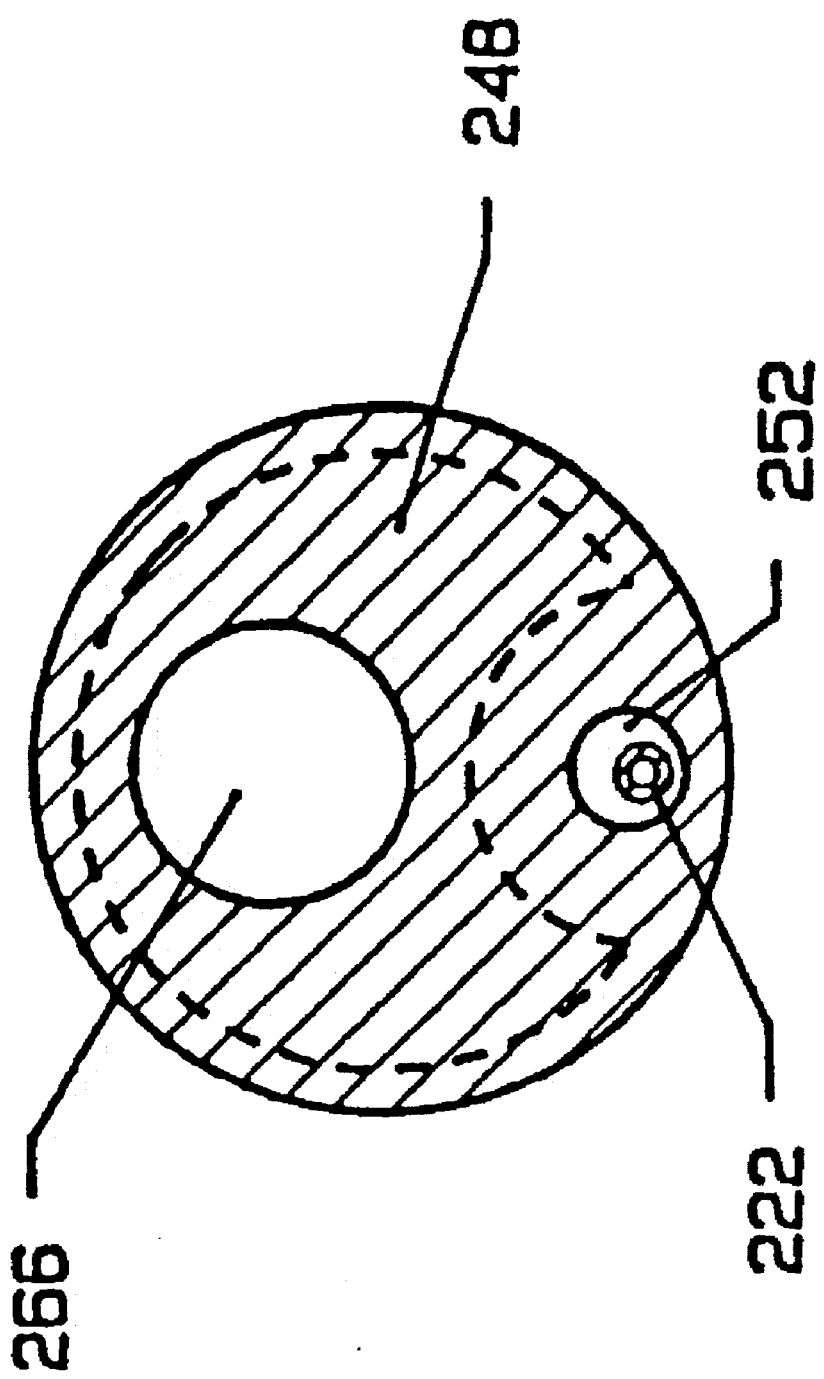
FIG. 27 is a transverse sectioned view of the catheter of FIG. 25.

FIG. 27 is a transverse sectioned view of atherectomy device 246 taken proximal to FIG. 26. All referenced elements are as previously described.

Figure 28:
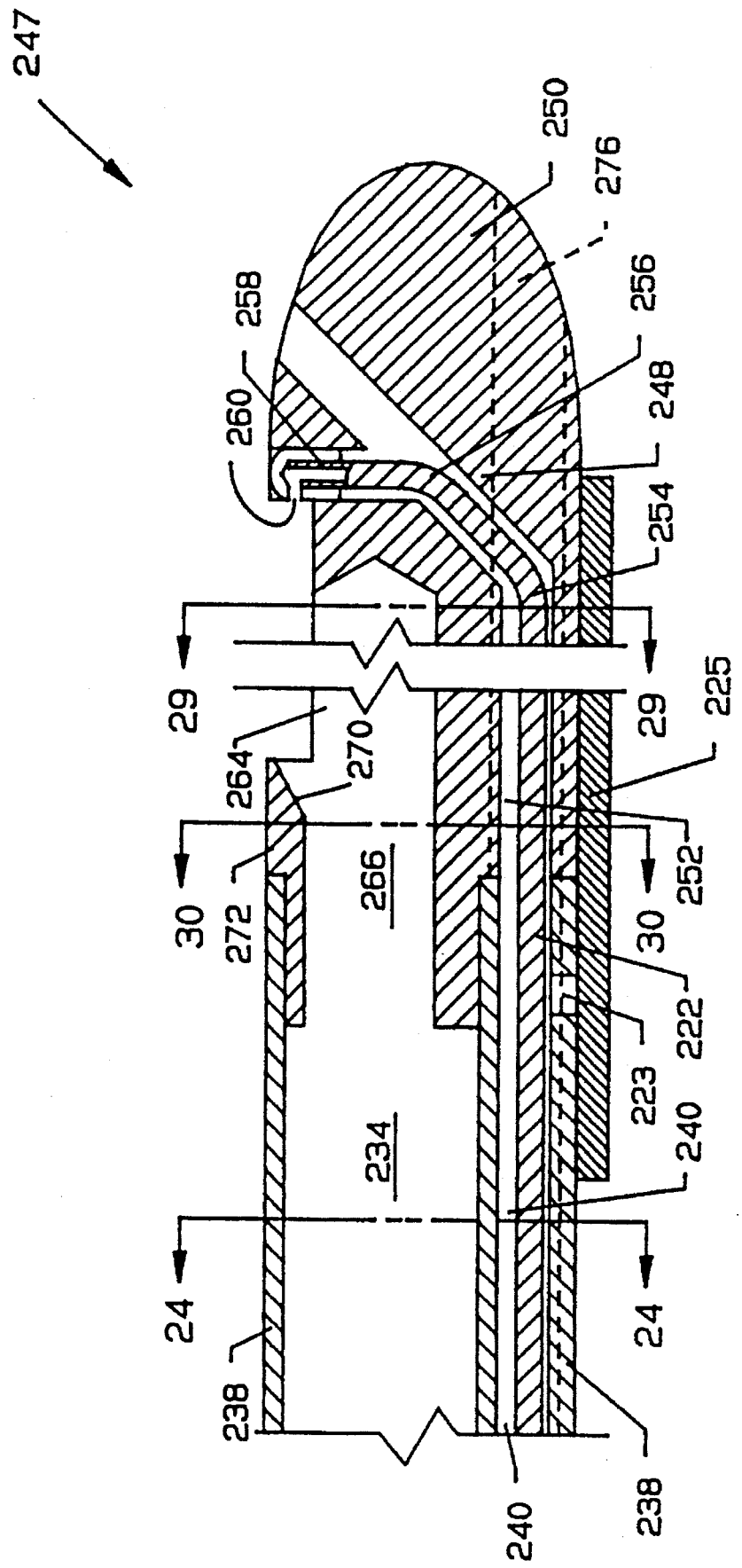
FIG. 28 is a longitudinal sectioned view of the distal end of a catheter employing an eighth embodiment of the present invention.

FIG. 28 is a longitudinal sectioned view of an atherectomy device 247 which is similar to atherectomy device 246, except that it has a guide wire lumen 276. All other referenced elements are as previously described. Balloon 225 is used to push the catheter against the deposit.

Figure 29:
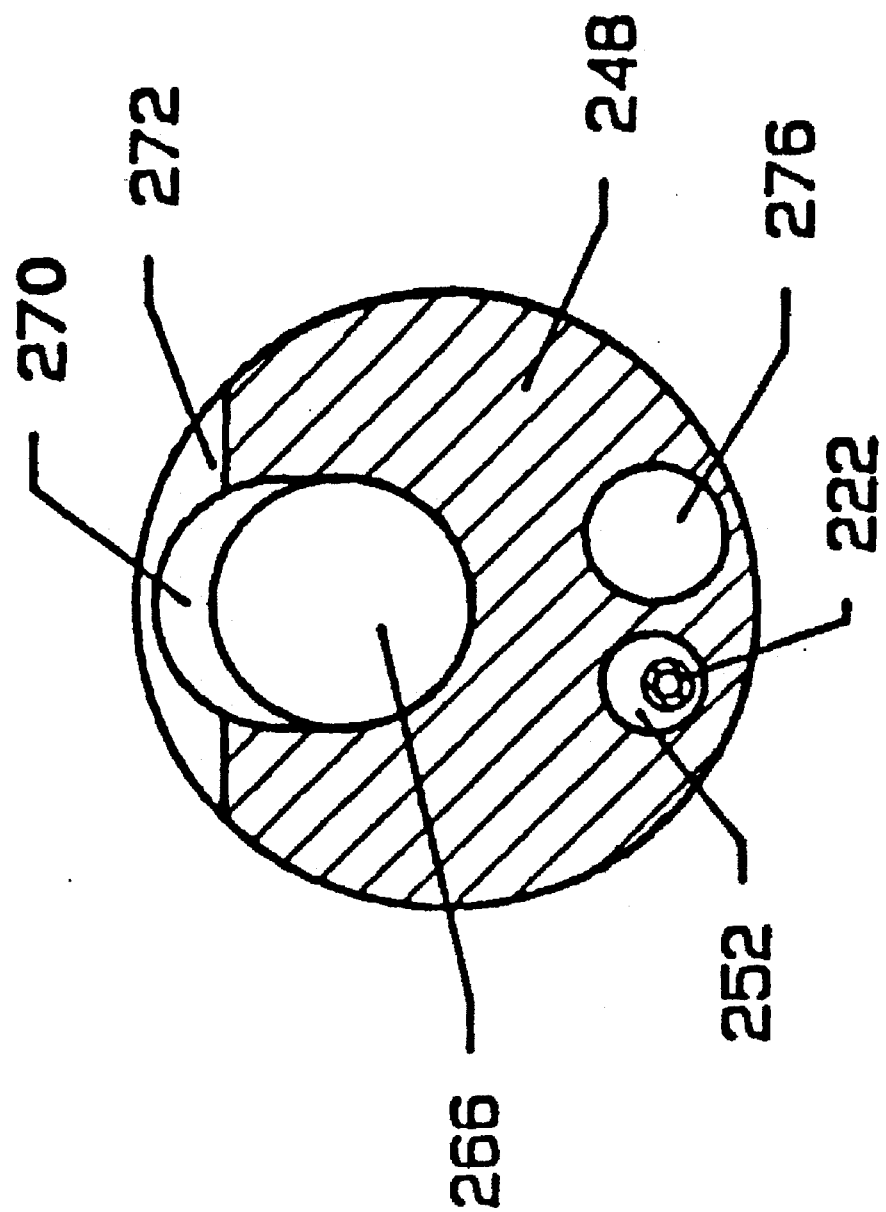
FIG. 29 is a transverse sectioned view of the catheter of FIG. 28.

FIG. 29 is a transverse sectioned view of the atherectomy device of FIG. 28. All referenced elements are as previously described.

Figure 30:
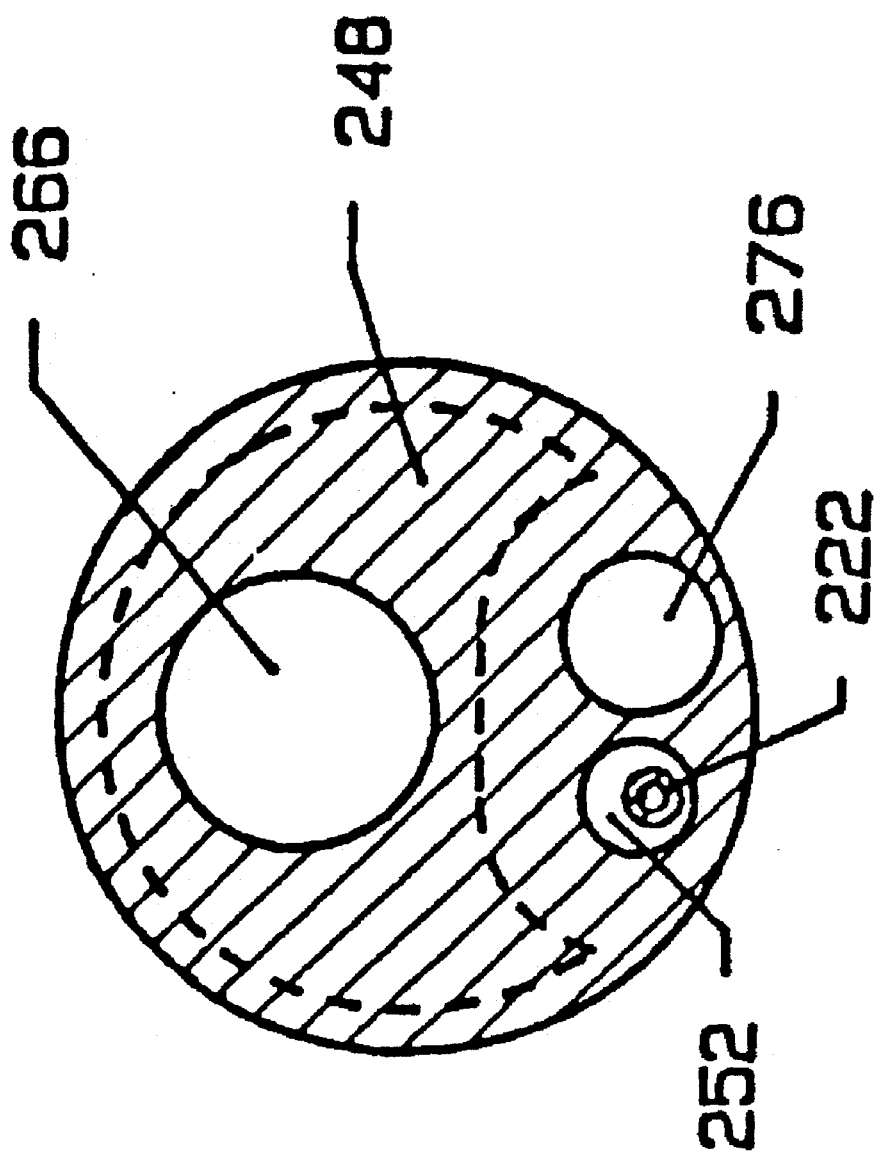
FIG. 30 is a transverse sectioned view of the catheter of FIG. 28.

FIG. 30 is a transverse sectioned view of the atherectomy device of FIG. 28 taken proximal to FIG. 29. All referenced elements are as previously described.

Figure 31:
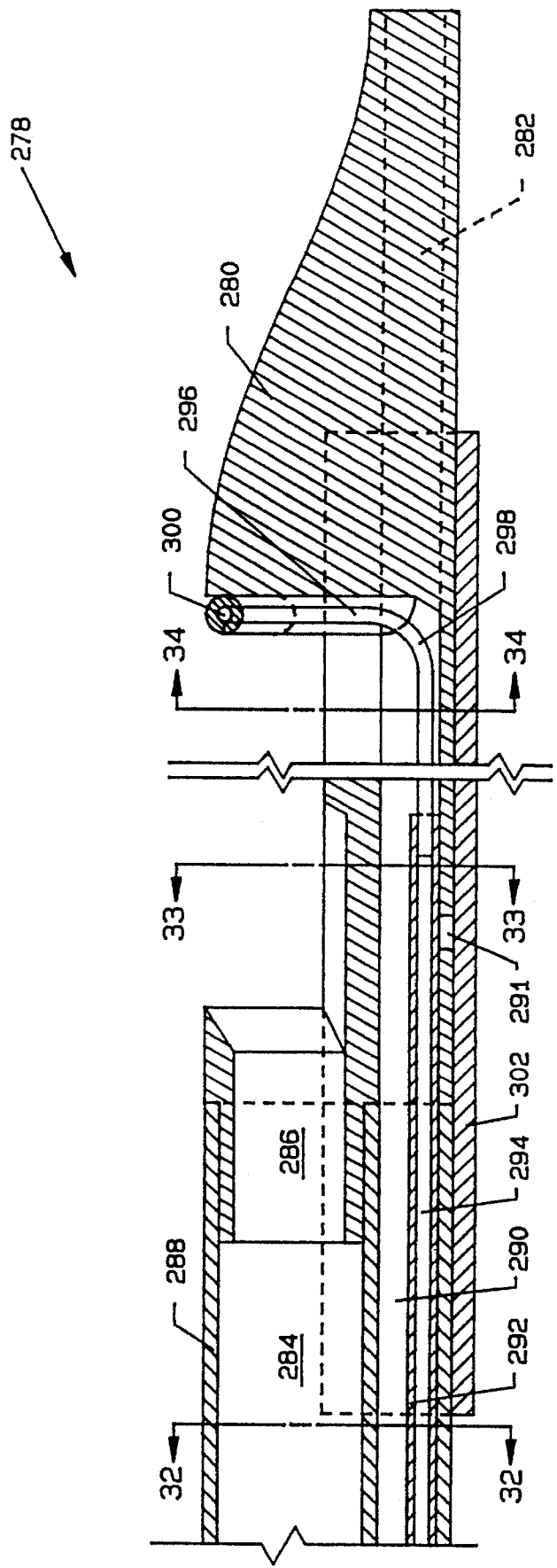
FIG. 31 is a longitudinal sectioned view of the distal end of a catheter employing a ninth embodiment of the present invention.

FIG. 31 is a longitudinal sectioned view of atherectomy device 278. Unlike previously discussed embodiments, atherectomy device 278 has multiple high pressure jets. This makes the device best suited to ablate the hardest of deposits near the arterial wall requiring the most aggressive and most precisely controlled high pressure saline streams.

Atherectomy device 278 has an extruded catheter body 288 having an evacuation lumen 284, a guide wire lumen 282, and a lumen 290 to accommodate hypo tubing 292. Lumen 290 is coupled to balloon inflation port 291 for inflation of balloon 302. Catheter body 288 is coupled to end member 280, which is molded to have an end evacuation lumen 286 and an area for receiving the deposit to be ablated. Hypo tubing 292 has an inner lumen 294 and a bend at point 298 to produce riser 296. Nozzle assembly 300, coupled to riser 296, has a plurality of high pressure jets as is described below.

Figure 32:
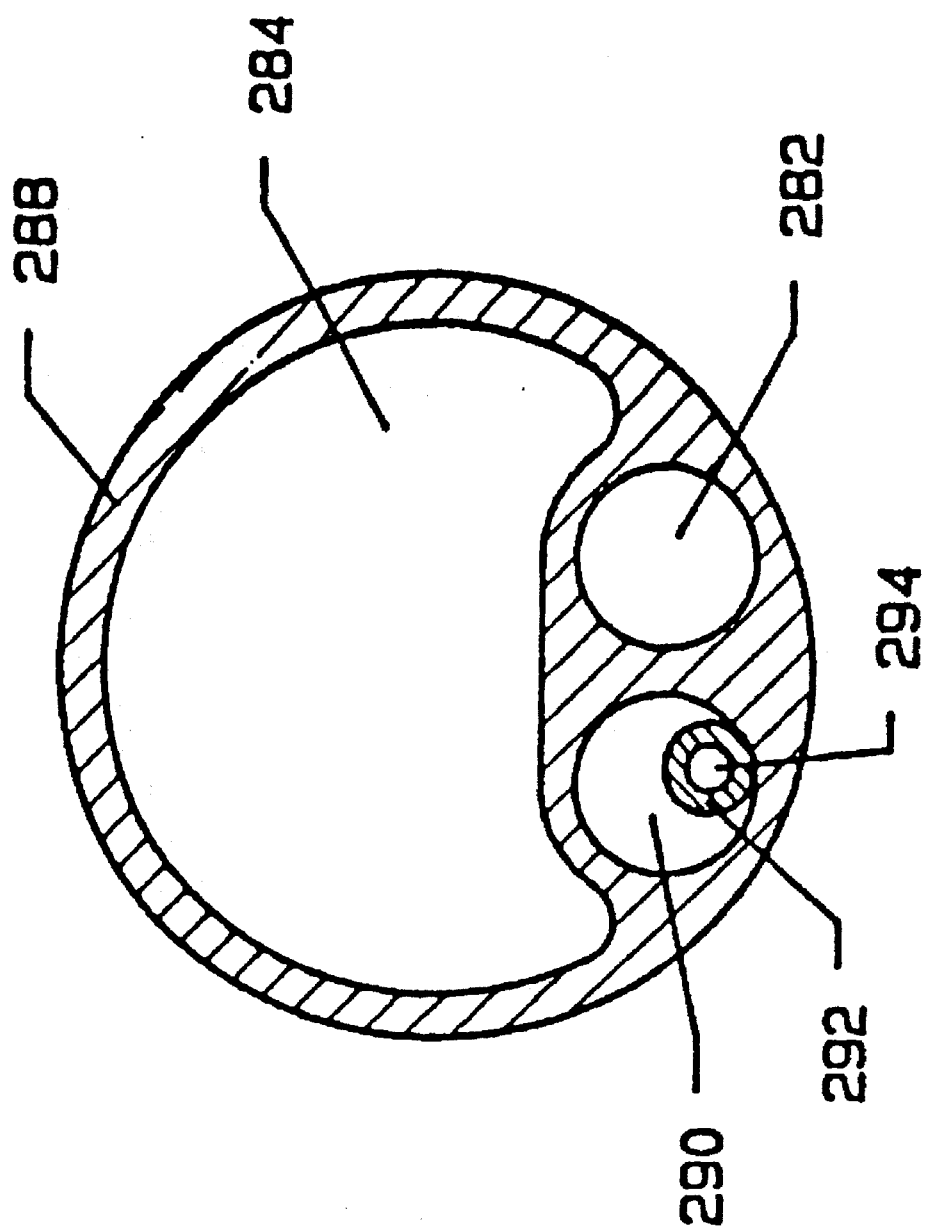
FIG. 32 is a transverse sectioned view of the catheter of FIG. 31.

FIG. 32 is a transverse sectioned view of atherectomy device 278 taken proximal to end member 280. All referenced elements are as previously described.

Figure 33:
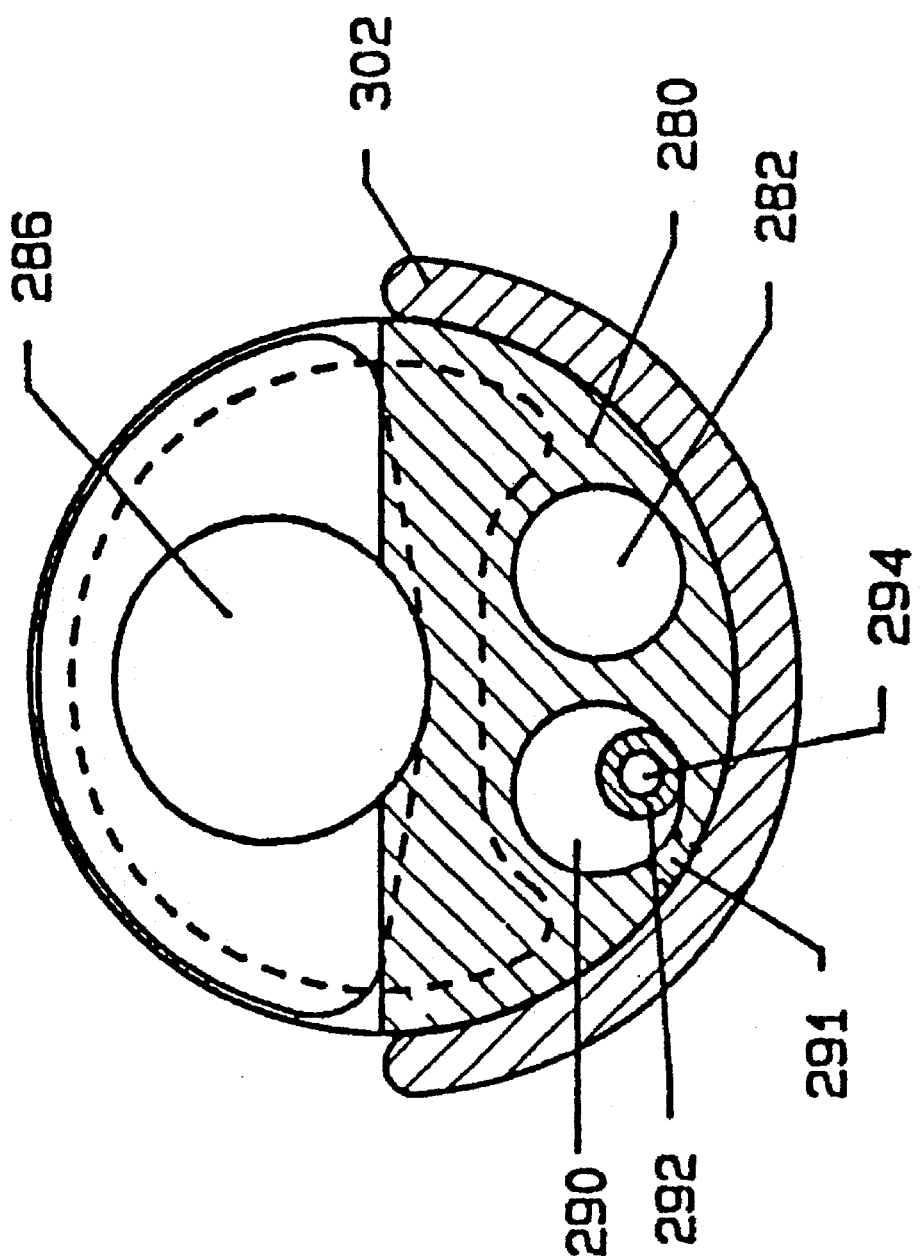
FIG. 33 is a transverse sectioned view of the catheter of FIG. 31.

FIG. 33 is a transverse sectioned view of atherectomy device 278 taken distal of FIG. 32. All referenced elements are as previously described.

Figure 34:
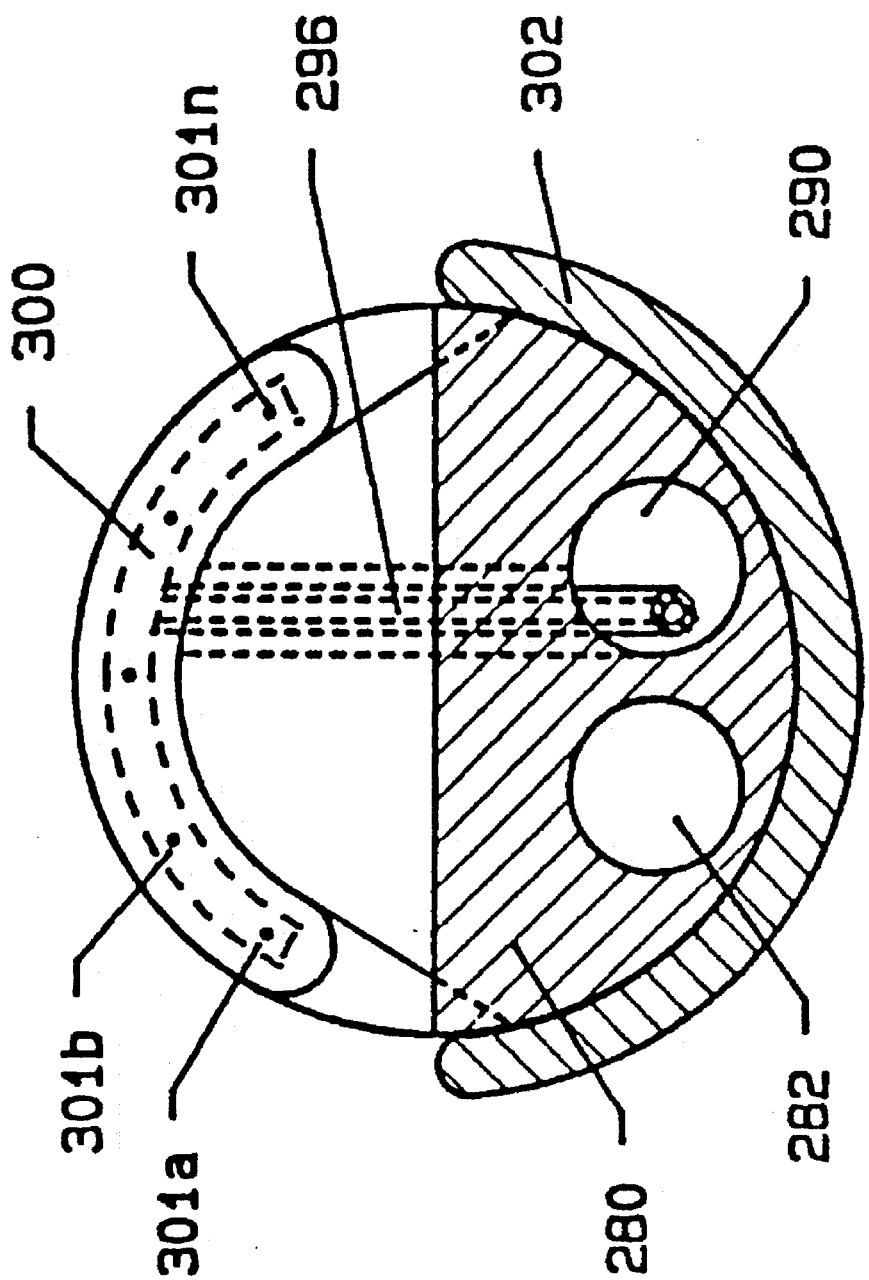
FIG. 34 is a transverse sectioned view of the catheter of FIG. 31.

FIG. 34 is a transverse sectioned view of atherectomy device 278 taken in a distal direction. Nozzle assembly 300 has a plurality of high pressure jets 301a–301n. All other referenced elements are as previously discussed.

Figure 35:
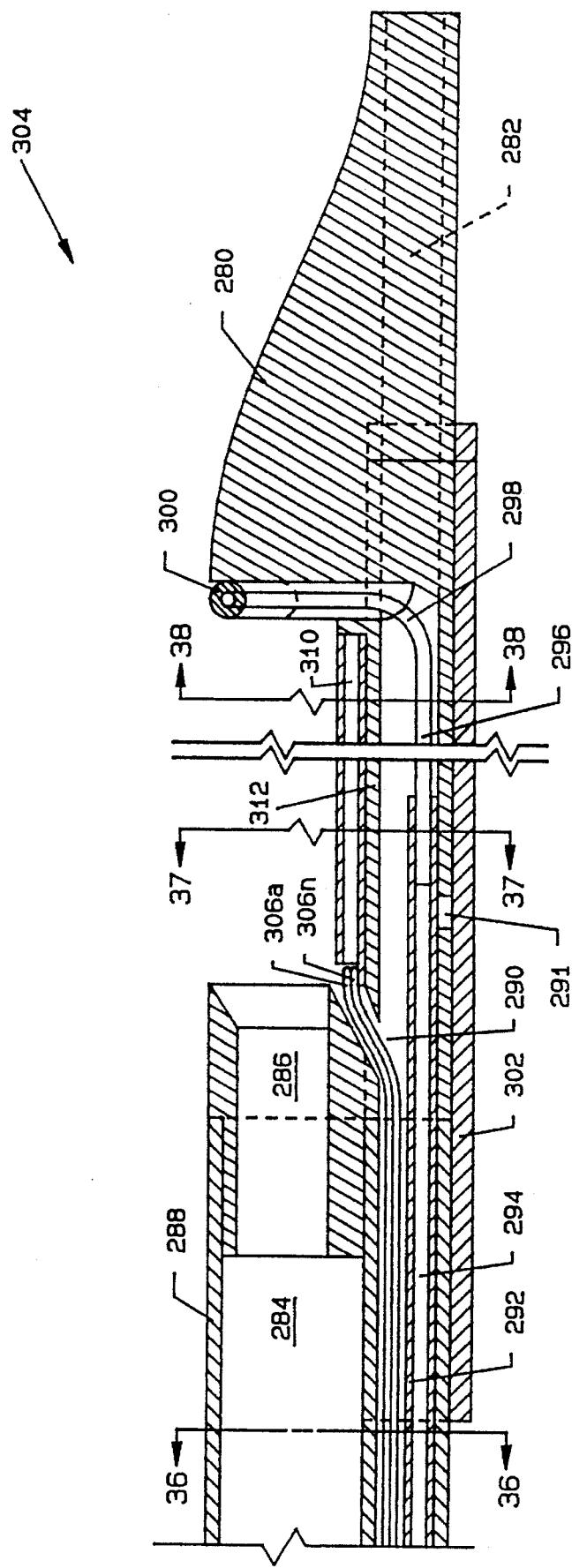
FIG. 35 is a longitudinal sectioned view of the distal end of a catheter employing a tenth embodiment of the present invention.

FIG. 35 is a longitudinal sectioned view of atherectomy device 304. It is similar to atherectomy device 278, except that it has ultrasonic transducer array 310 mounted on array mounting surface 312. Each element of ultrasonic transducer array 310 is separately coupled to ultrasonic monitor 60 (see also FIG. 1B) via a different one of cables 306a–306n. All other referenced elements are as previously described. Balloon inflation port 291 is coupled to lumen 290 for inflation of balloon 302.

Figure 36:
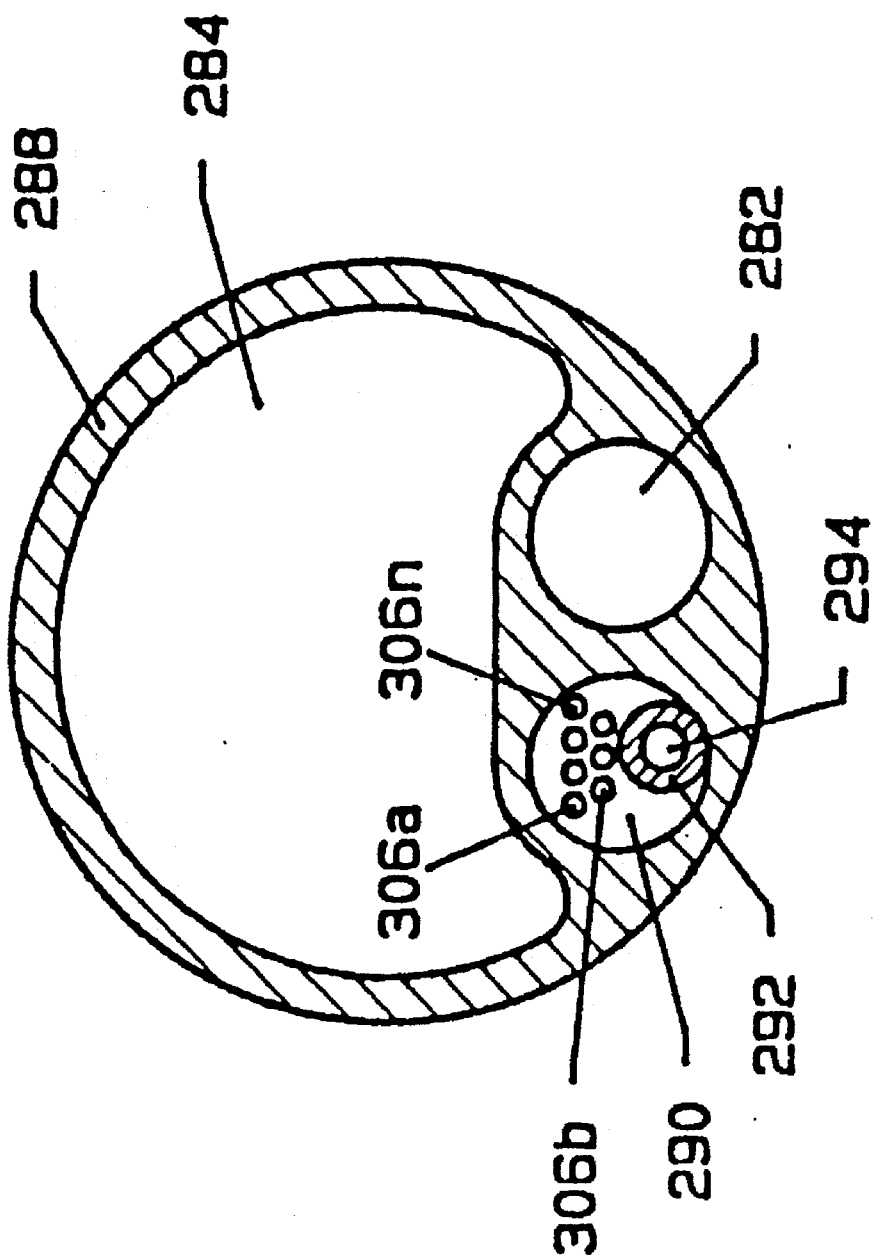
FIG. 36 is a transverse sectioned view of the catheter of FIG. 35.

FIG. 36 is a transverse sectioned view of atherectomy device 304. All referenced elements are as previously described. Note that cables 306a–306n share lumen 290 with hypo tubing 292.

Figure 37:
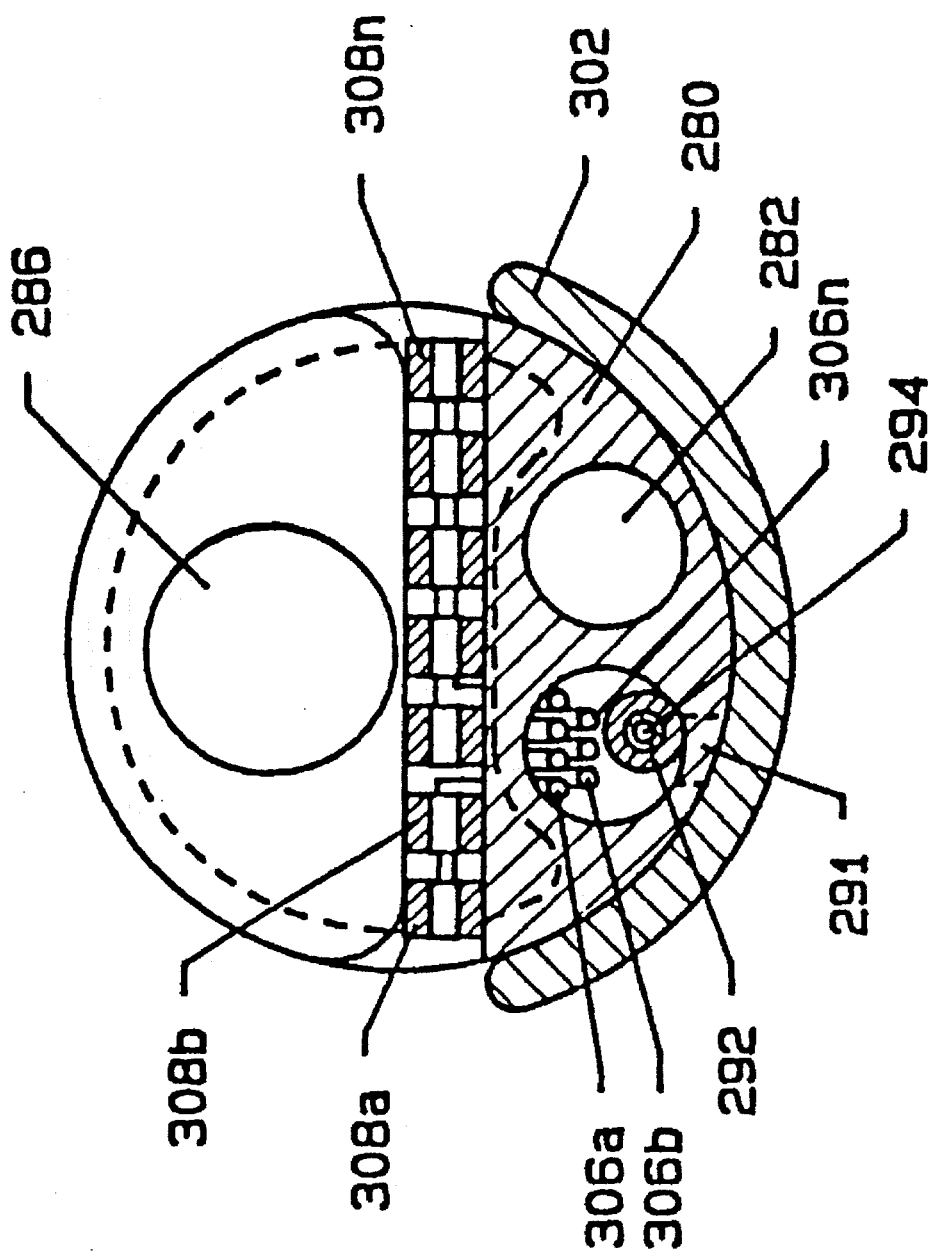
FIG. 37 is a transverse sectioned view of the catheter of FIG. 35.

FIG. 37 is a transverse sectioned view of atherectomy device 304 taken distal to FIG. 36. All referenced elements are as previously described. Ultrasonic transducer array 310 comprises separate ultrasonic transducers 308a–308n.

Figure 38:
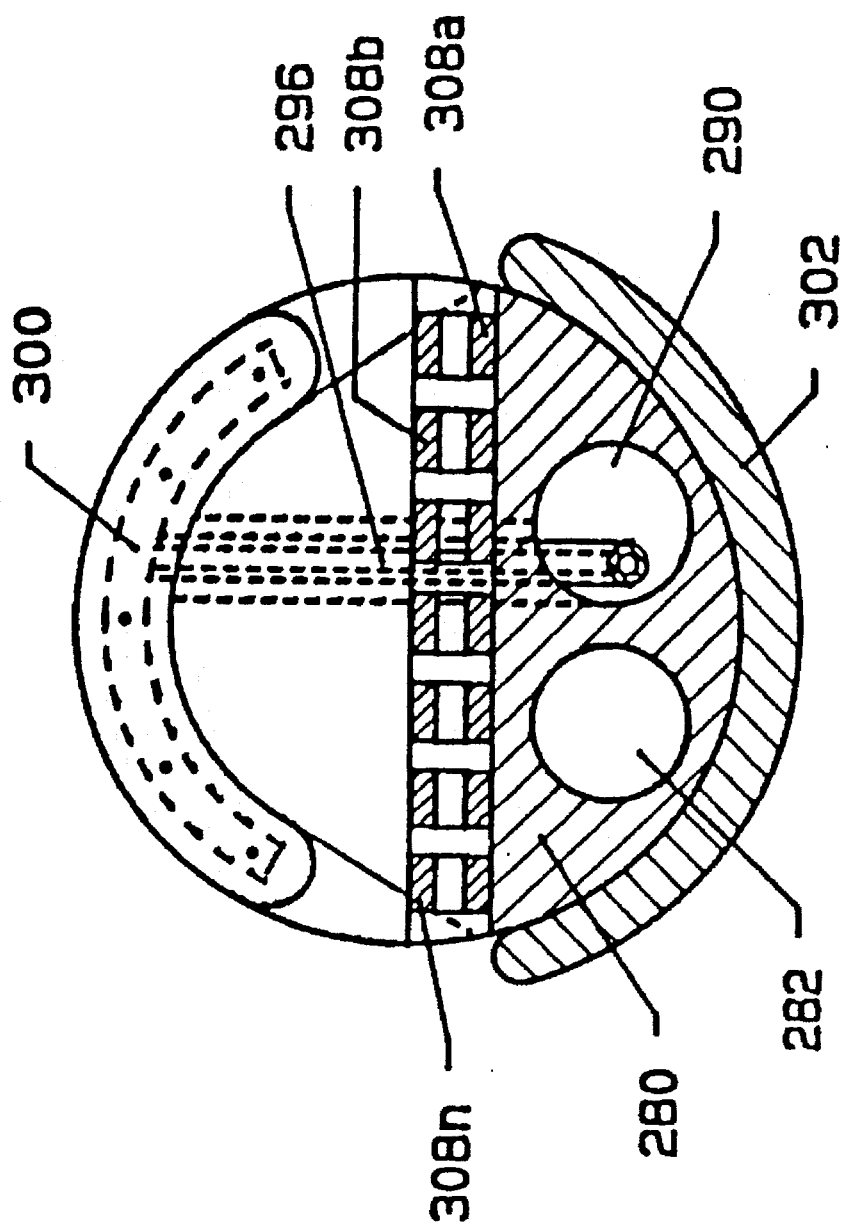
FIG. 38 is a transverse sectioned view of the catheter of FIG. 35.

FIG. 38 is a transverse sectioned view of atherectomy device 304 taken in a distal direction. All referenced elements are as previously described.

Figure 39:
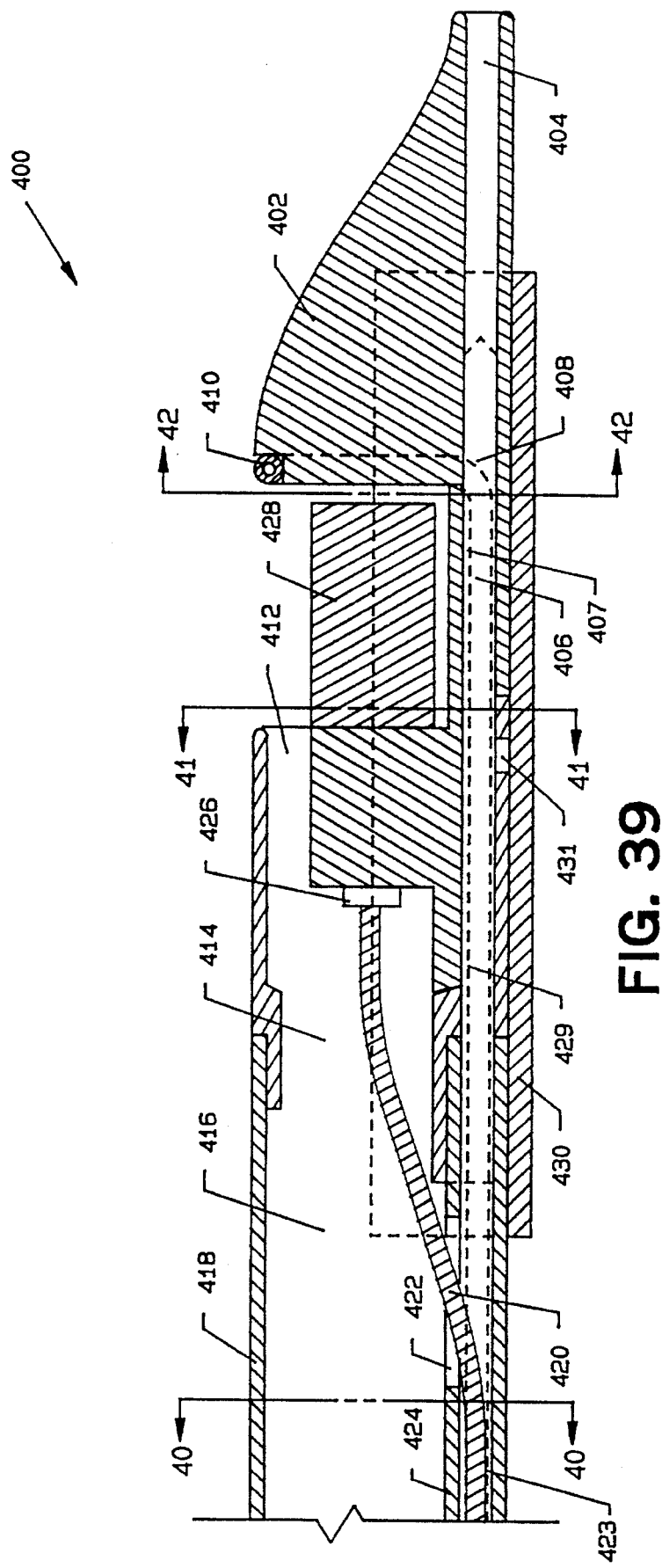
FIG. 39 is a longitudinal sectioned view of the distal end of a catheter employing an eleventh embodiment of the present invention.

FIG. 39 is a transverse sectioned view of atherectomy device 400 where all numerals correspond to those elements previously described. It is similar in construction and operation to atherectomy device 304, except that it has an integrated ultrasonic transducer assembly 428. This permits a differently constructed catheter having a relatively larger evacuation lumen 416. Ultrasonic transducer assembly 428 is internally multiplexed such that a single cable 420, coupled via connector 426, is sufficient to communicate with ultrasonic monitor 60 (see also FIG. 1B). Cable 420 passes through a separate lumen 423 of catheter body 418 and to connector 426 via port 422.

Balloon inflation lumen 429 is coupled to balloon inflation port 431 and is used to inflate balloon 430. Lumen 404, which extends through end member 402, provides for use with a guide wire. End evacuation lumen 414 couples evacuation port 412 to evacuation lumen 416 of catheter body 418. Nozzle assembly 410 is coupled to hypo tubing 406, which bends at point 408 as shown Hypo tubing 406 aligns in lumen 407.

Figure 40:
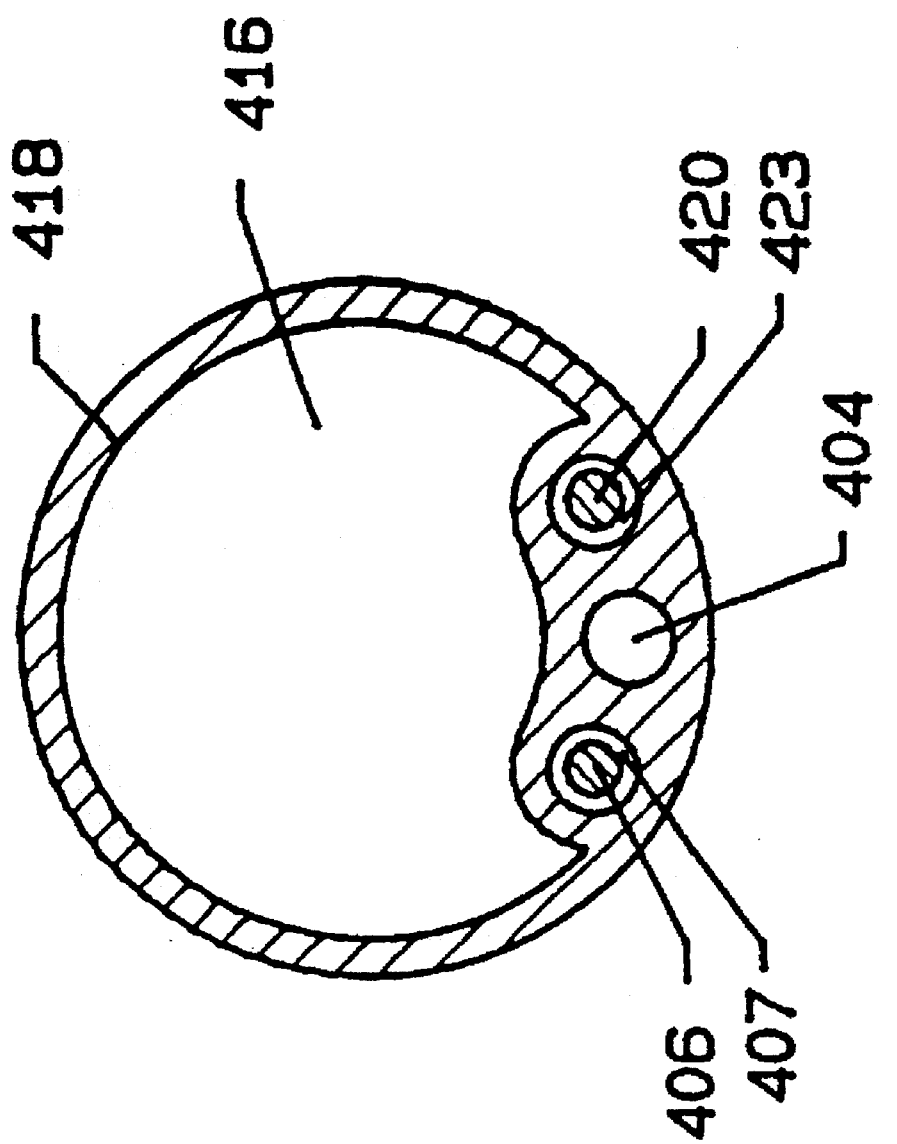
FIG. 40 is a transverse sectioned view of the catheter of FIG. 39.

FIG. 40 is a transverse sectioned view of atherectomy device 400. All referenced elements are as previously described.

Figure 41:
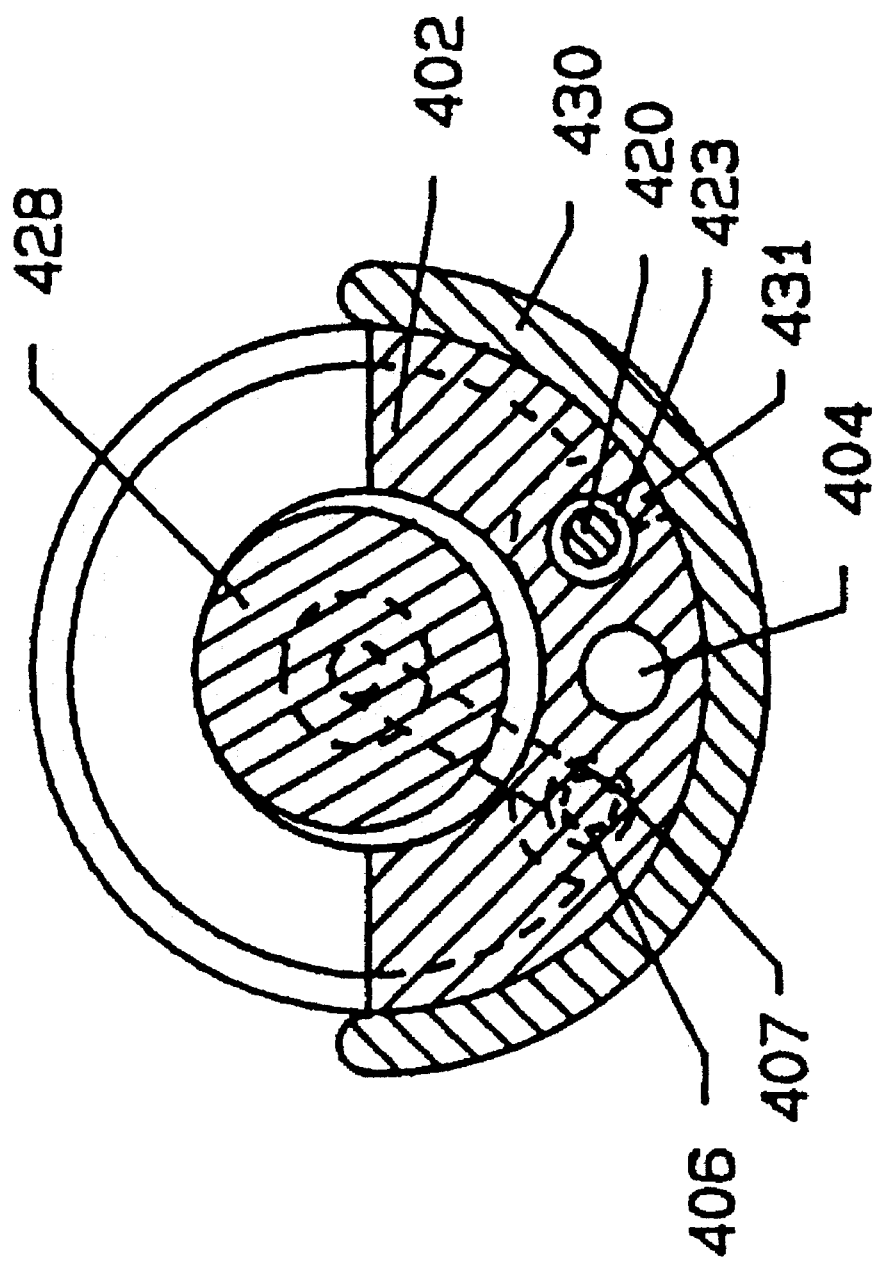
FIG. 41 is a transverse sectioned view of the catheter of FIG. 39.

FIG. 41 is a transverse sectioned view of atherectomy device 400 taken distal of FIG. 40. All referenced elements are as previously referenced.

Figure 42:
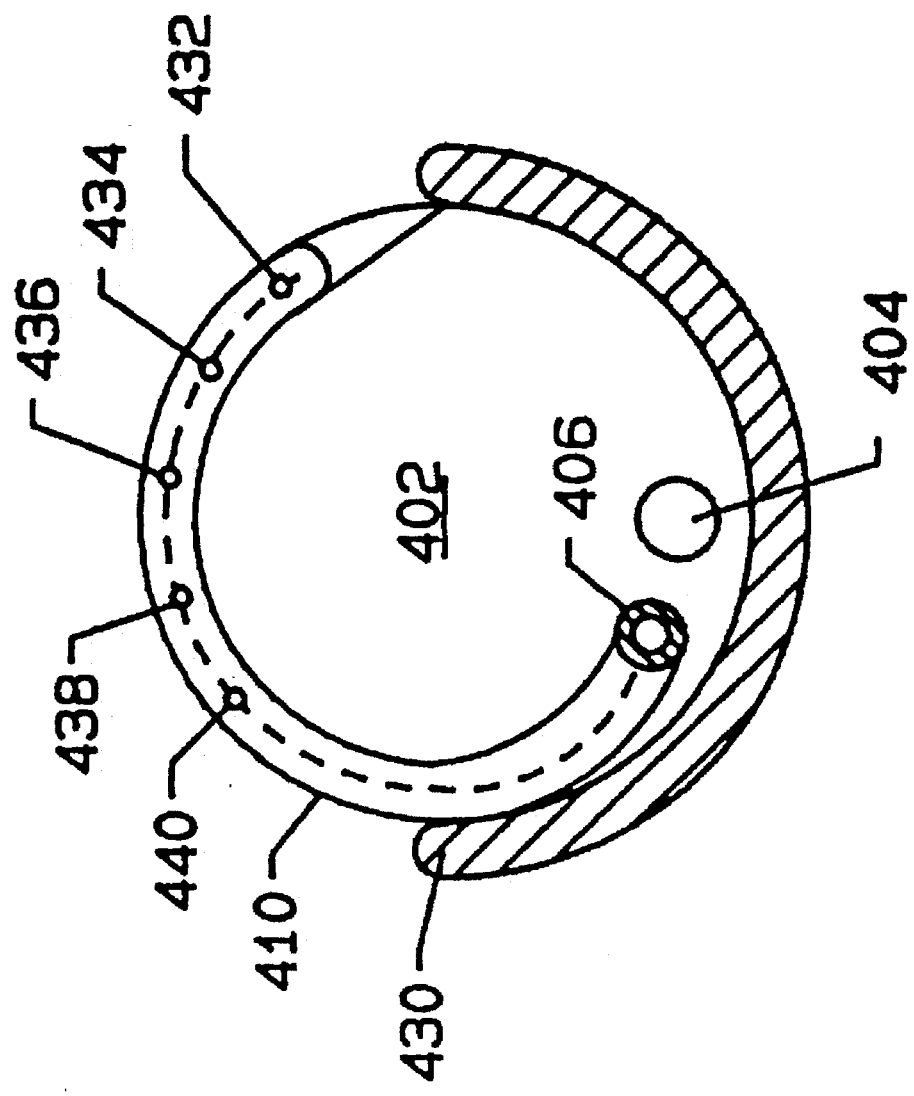
FIG. 42 is a transverse sectioned view of the catheter of FIG. 39.

FIG. 42 is a transverse sectioned view of atherectomy device 400 taken in a distal direction. All referenced elements are as previously described. Nozzle assembly 410 has individual high pressure jets 432, 434, 436, 438, and 440.

Figure 43:
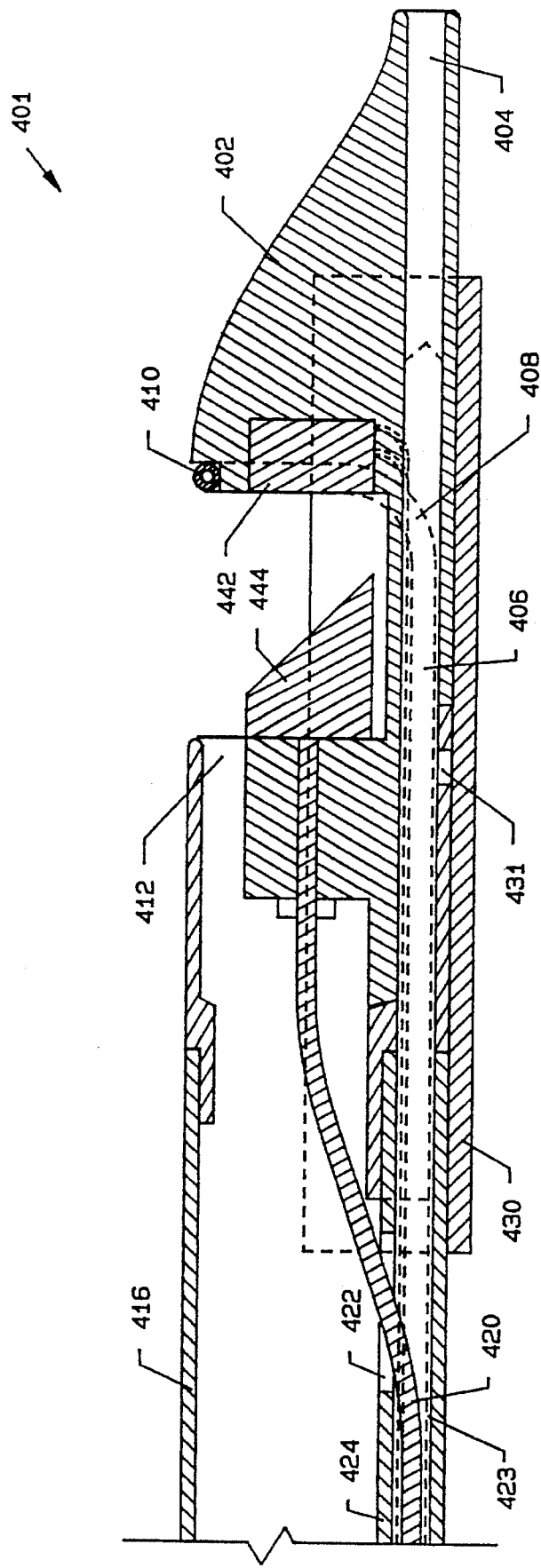
FIG. 43 is a longitudinal sectioned view of the distal end of a catheter employing a twelfth embodiment of the present invention.

FIG. 43 is a longitudinal sectioned view of an atherectomy device 401 which is similar to atherectomy device 400, except that ultrasonic transducer assembly 442 and ultrasonic mirror 444 replace ultrasonic transducer assembly 428 of atherectomy device 400. This particular embodiment is slightly more complex to construct, but has the advantage of a larger area to accommodate the deposit to be ablated. Balloon inflation port 431 is used to inflate balloon 430 All numerals correspond to those elements previously described.

Figure 44:
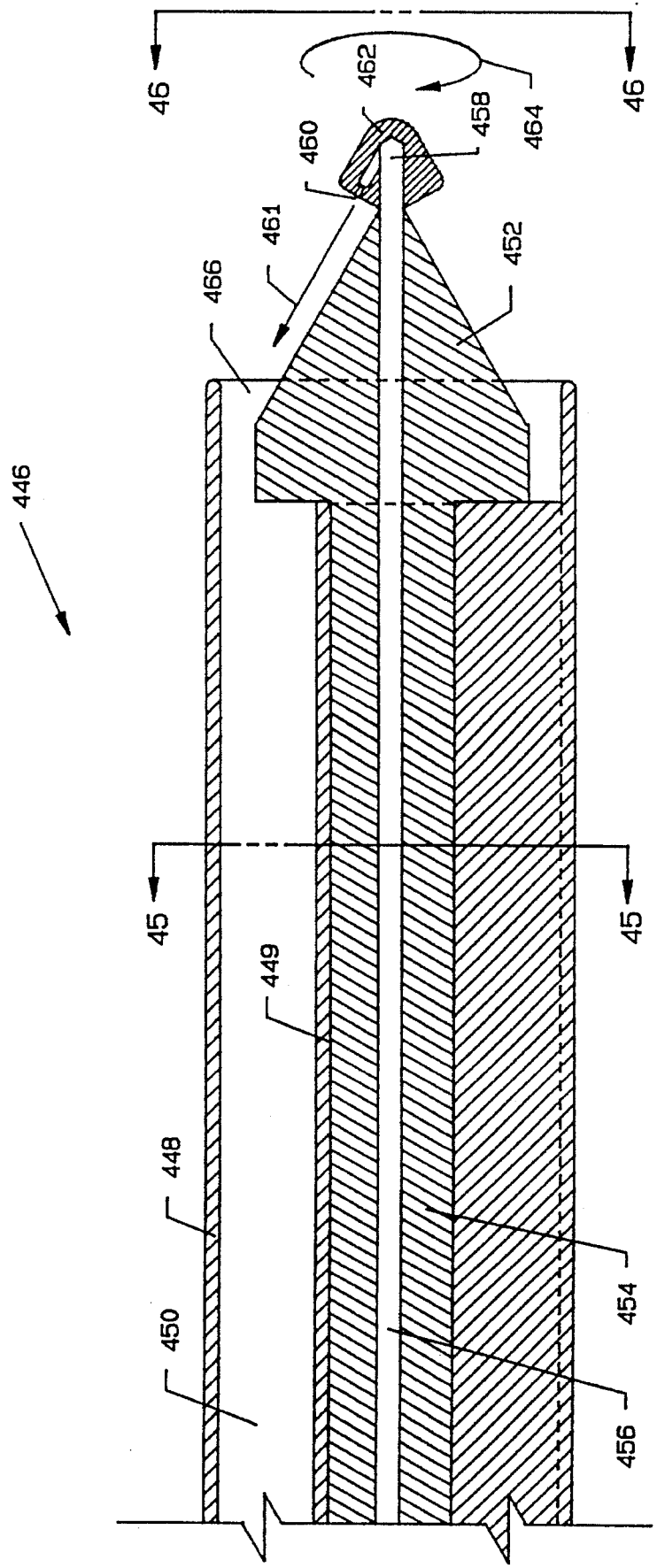
FIG. 44 is a longitudinal sectioned view of the distal end of a catheter employing a thirteenth embodiment of the present invention.

FIG. 44 is a longitudinally sectioned view of the distal end of an atherectomy catheter 446. It has an extruded outer catheter body 448 containing several lumens (see also FIG. 45). The central lumen 449 contains sensor positioning rod 454, which is a flexible torque transmitting device used to rotate ultrasonic transducer 452 in the direction of or opposite to arrow 464. In this way, ultrasonic transducer 452 may be radially directed to monitor the desired portion of the vessel lumen. A lumen 456 extends centrally through the sensor positioning rod 454 and connects to a distal tip 458 in a nozzle assembly 462.

Attached to the distal end of ultrasonic transducer 452 is distal tip 458 containing the nozzle assembly 462 for distribution of high pressure fluid from lumen 456. High pressure jet 460 of nozzle assembly 462 is directed proximally and radially outward. It produces a high pressure stream of fluid which proceeds in the direction of arrow 461. Because nozzle assembly 462 is coupled to ultrasonic transducer 452, rotation of positioning rod 454 also radially positions high pressure jet 460.

The high pressure stream of fluid is directed toward fluid evacuation port 466 to assist in evacuation of particulate matter as the deposit is ablated. With high pressure jet 460 directed along arrow 461, particulate matter is evacuated via evacuation lumen 450. Two other evacuation lumens position starting at the evacuation port 466 (see also FIG. 45) to provide for evacuation as nozzle assembly 462 is rotated.

Figure 45:
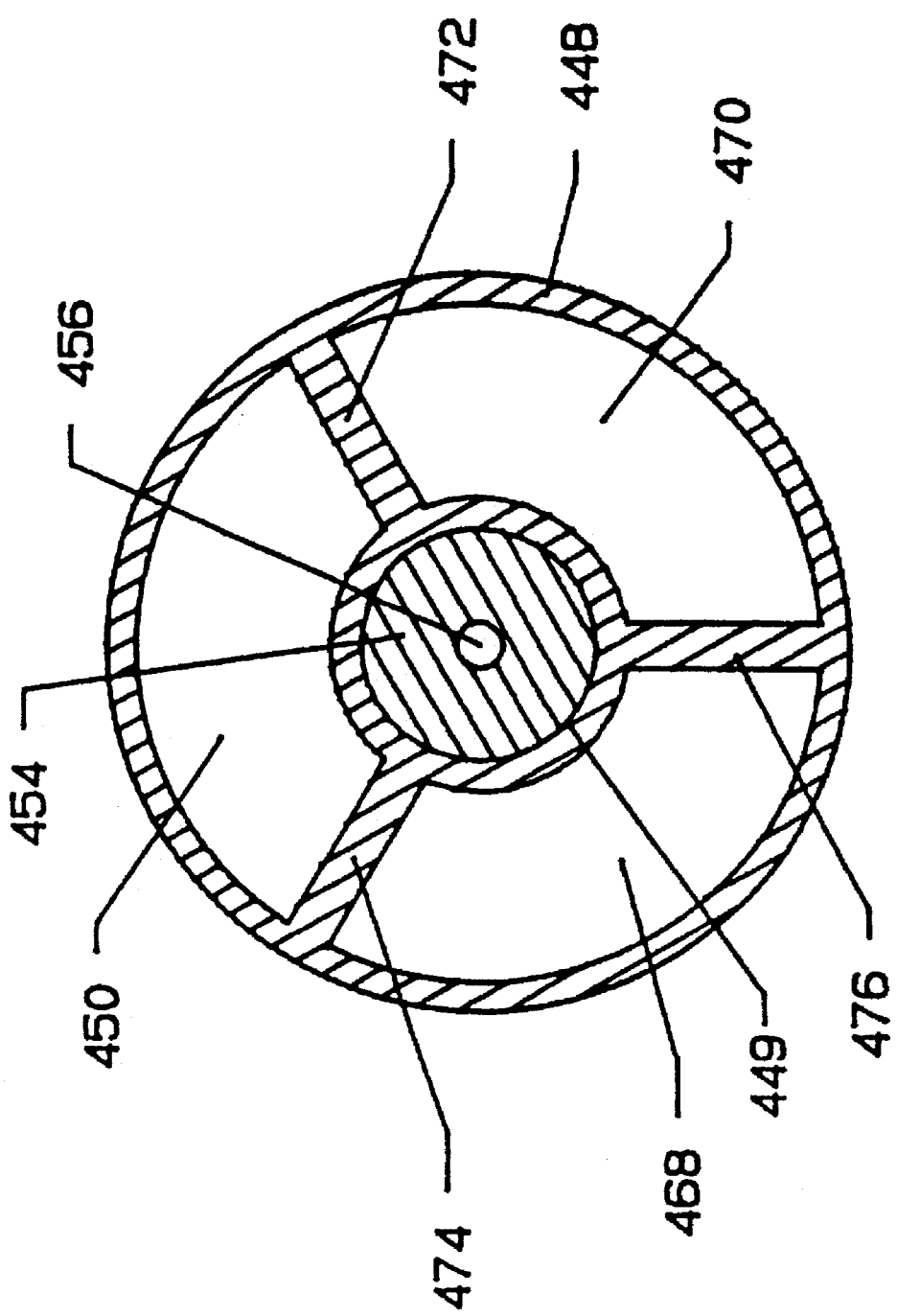
FIG. 45 is a transverse sectioned view of the catheter of FIG. 44.

FIG. 45 is a transverse sectioned view of atherectomy catheter 446. Lumens 450, 468, and 470 are all evacuation lumens. The selection of which evacuation lumen is used at any particular point in time depends upon the radial attitude of nozzle assembly 462 (see also FIG. 44). The three individual evacuation lumens are separated by septums 472, 474, and 476.

Figure 46:
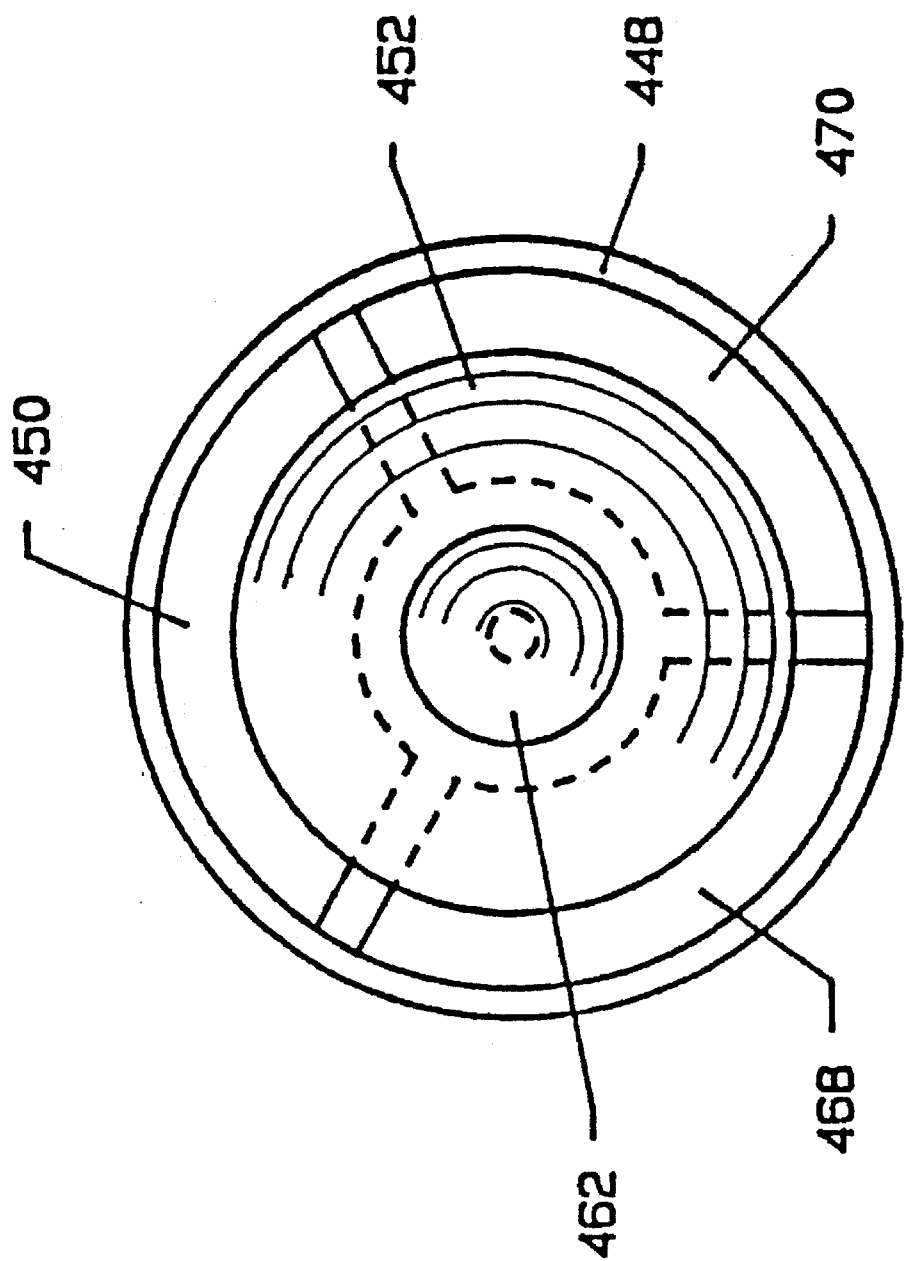
FIG. 46 is an end view of the catheter of FIG. 44.

FIG. 46 is an end view of atherectomy catheter 446. All referenced elements are as previously discussed.

Having thus described the preferred embodiments of the present invention, those of skill in the art will readily appreciate that additional embodiments may be made from the teachings found herein within the scope of the claims hereto attached.

We claim:

1. An apparatus for ablating at least a portion of a deposit within a vessel of a patient comprising:

a. catheter having a proximal end and a distal end;
   b. a working fluid;
   c. means coupled to said proximal end of said catheter for supplying said working fluid under high pressure;
   d. means coupled to said distal end of said catheter for directing said working fluid in the form of a stream at a deposit within a vessel of a patient, said means for supplying said working fluid under high pressure and said means for directing said working fluid in the form of a stream being capable of supplying and directing said working fluid at a velocity high enough to generate a stagnation pressure sufficient to remove ablated deposit debris without the use of a vacuum; and,
   e. target means coupled to said distal end of said catheter at a location longitudinally spaced from said directing means for preventing said working fluid from directly impinging upon a vessel of a patient; said longitudinal spacing being sufficient to accommodate at least a portion of deposit being ablated.

2. An apparatus according to claim 1 wherein said working fluid is a saline solution.

3. An apparatus according to claim 2 wherein said target means is positioned with respect to said directing means such that in use said target means can be interposed between said directing means and a vessel of a patient.

4. An apparatus according to claim 3 wherein said directing means comprises a plurality of high pressure jets.

5. An apparatus according to claim 1 wherein said directing means comprises a plurality of high pressure jets.

6. An apparatus according to claim 1 wherein said directing means comprises a high pressure jet.

7. An apparatus according to claim 6 wherein said target is distal to said directing means.

8. An apparatus according to claim 6 wherein said directing means is distal to said target.

9. An apparatus according to any one of claims 1, 2, 3, 6, 4 or 5 further comprising an ultrasonic transducer array coupled to said distal end of said catheter.

10. An apparatus according to claim 9 wherein said ultrasonic transducer array is oriented at said distal end of said catheter such that when it is inserted into a vessel of a patient, it will be directed toward the vessel or a deposit within the vessel.

11. An apparatus according to claim 9 further comprising a reflecting device toward which said ultrasonic transducer array is directed.

12. An apparatus according to claim 9 further comprising means coupled to said distal end of said catheter for evacuating particulate matter ablated from the deposit.

13. An apparatus according to claim 12 wherein said evacuating means comprises an evacuation lumen toward which said stream of said working fluid is directed.

14. An apparatus according to claim 13 further comprising an inflatable balloon for positioning said distal end of said catheter in the vessel.

15. An apparatus according to any one of claims 1, 2, 3 or 6 wherein said directing means is oriented to direct said working fluid in the form of a stream parallel to the longitudinal axis of said catheter.

16. An apparatus according to claim 15 further comprising an ultrasonic transducer array coupled to said distal end of said catheter.

17. An apparatus according to claim 15 further comprising means coupled to said distal end of said catheter for evacuating particulate matter ablated from the deposit.

18. An apparatus according to claim 17 wherein said evacuating means comprises an evacuation lumen toward which said stream of said working fluid is directed.

19. An apparatus according to claim 18 further comprising an inflatable balloon for positioning said distal end of said catheter in the vessel.

20. An apparatus according to any one of claims 1, 2, 3, 6, 4 or 5 further comprising means coupled to said distal end of said catheter for evacuating particular matter ablated from a deposit within a vessel of a patient.

21. An apparatus according to claim 20 wherein said evacuating means comprises an evacuation lumen toward which said stream of said working fluid is directed.

22. An apparatus according to claim 21 further comprising an inflatable balloon for positioning said distal end of said catheter in the vessel.

23. An apparatus according to any one of claims 1, 2, 3, 6, 4 or 5 wherein said target means comprises means coupled to said distal end of said catheter for evacuating particulate matter ablated from the deposit.

24. An apparatus according to any one of claims 1, 2, 3 or 6 wherein said directing means is oriented to direct said working fluid in the form of a stream nonparallel to the longitudinal axis of said catheter.

25. An apparatus according to claim 24 further comprising means coupled to said distal end of said catheter for evacuating particulate matter ablated from a deposit within a vessel of a patient.

26. An apparatus according to claim 25 wherein said evacuating means comprises an evacuation lumen toward which said stream of said working fluid is directed.

27. An apparatus according to claim 26 further comprising an inflatable balloon for positioning said distal end of said catheter in the vessel.

28. An apparatus according to claim 24 further comprising an ultrasonic transducer array coupled to said distal end of said catheter.

29. In a method for ablating at least a portion of a deposit in a vessel of a patient by advancing a catheter with a proximal end and a distal end into the vessel until said distal end of said catheter is positioned at the site of the deposit, supplying pressurized fluid to the catheter, and using this fluid to create a stream which impinges upon the deposit to ablate the deposit, the improvements comprising:

a. applying said stream at a velocity high enough to generate a stagnation pressure sufficient to remove deposit debris without the use of a vacuum; and, b. interposing a target intermediate said stream of fluid and the vessel to protect the vessel from said stream yet provided space to accommodate at least a portion of the deposit.

30. The method of claim 29 further comprising monitoring said ablating with an ultrasonic transducer array coupled to said distal end of said catheter.

31. The method of claim 29 wherein said stream of fluid is directed away from said proximal end of said catheter.

32. The method of claim 29 wherein said pressurized fluid is supplied at a pressure within the range of 5,000 to 50,000 psi.

33. The method of claim 29 wherein said pressurized fluid is supplied at a pressure of about 30,000 psi.

* * * * *